US009688605B2

(12) United States Patent
McGuiness

(10) Patent No.: US 9,688,605 B2
(45) Date of Patent: Jun. 27, 2017

(54) ORGANIC SALTS OF GLYCERIDE-CYCLIC CARBOXYLIC ACID ANHYDRIDE ADDUCTS AS CORROSION INHIBITORS

(71) Applicant: The Lubrizol Corporation, Wickliffe, OH (US)

(72) Inventor: Mark J. McGuiness, Chagrin Falls, OH (US)

(73) Assignee: THE LUBRIZOL CORPORATION, Wickliffe, OH (US)

( * ) Notice: Subject to any disclaimer, the term of this patent is extended or adjusted under 35 U.S.C. 154(b) by 0 days.

(21) Appl. No.: 15/103,119

(22) PCT Filed: Dec. 5, 2014

(86) PCT No.: PCT/US2014/068707
§ 371 (c)(1),
(2) Date: Jun. 9, 2016

(87) PCT Pub. No.: WO2015/088893
PCT Pub. Date: Jun. 18, 2015

(65) Prior Publication Data
US 2016/0311755 A1    Oct. 27, 2016

Related U.S. Application Data

(60) Provisional application No. 61/913,982, filed on Dec. 10, 2013.

(51) Int. Cl.
| C07C 69/75 | (2006.01) |
| C07C 69/40 | (2006.01) |
| C07C 69/593 | (2006.01) |
| C07C 217/08 | (2006.01) |
| C10L 10/04 | (2006.01) |
| C23F 11/10 | (2006.01) |
| C23F 11/12 | (2006.01) |
| C23F 11/14 | (2006.01) |
| C07C 211/63 | (2006.01) |
| C07C 215/40 | (2006.01) |
| B05D 7/00 | (2006.01) |
| C09D 5/08 | (2006.01) |

(52) U.S. Cl.
CPC .............. *C07C 69/75* (2013.01); *B05D 7/00* (2013.01); *C07C 69/40* (2013.01); *C07C 69/593* (2013.01); *C07C 211/63* (2013.01); *C07C 215/40* (2013.01); *C07C 217/08* (2013.01); *C09D 5/086* (2013.01); *C10L 10/04* (2013.01); *C23F 11/10* (2013.01); *C23F 11/128* (2013.01); *C23F 11/143* (2013.01); *C07C 2101/14* (2013.01); *C10N 2230/12* (2013.01)

(58) Field of Classification Search
CPC .......... B05D 7/00; C09D 5/086; C07C 69/40; C07C 69/593; C07C 69/75; C07C 217/08; C07C 211/63; C07C 215/40; C07C 2110/14; C23F 11/128; C23F 11/143
See application file for complete search history.

(56) References Cited

U.S. PATENT DOCUMENTS

| 2,000,717 A | 5/1935 | Roberts et al. |
| 2,044,747 A | 6/1936 | Ott et al. |
| 2,459,176 A | 1/1949 | Moore et al. |
| 2,559,466 A | 7/1951 | Root et al. |
| 2,616,904 A | 11/1952 | Alan et al. |
| 2,695,910 A | 11/1954 | Asseff et al. |
| 2,767,164 A | 10/1956 | Alan et al. |
| 2,767,209 A | 10/1956 | Rhodes et al. |
| 2,798,852 A | 7/1957 | Wierber et al. |
| 2,959,551 A | 11/1960 | Le |
| 3,106,538 A | 10/1963 | Broadhead et al. |
| 3,147,232 A | 9/1964 | Le et al. |
| 3,219,666 A | 11/1965 | Norman |
| 3,274,135 A | 9/1966 | Le et al. |
| 3,293,272 A | 12/1966 | Freund |
| 3,565,804 A | 2/1971 | Anderson et al. |
| 3,697,574 A | 10/1972 | Karll et al. |
| 3,736,357 A | 5/1973 | Karll et al. |
| 3,873,465 A | 3/1975 | Di Simone |
| 3,878,231 A | 4/1975 | Harwood |
| 3,932,303 A | 1/1976 | Hollingshad |
| 4,066,398 A | 1/1978 | Hwa |
| 4,148,605 A | 4/1979 | Andress, Jr. |
| 4,234,435 A | 11/1980 | Meinhardt |
| 4,263,216 A | 4/1981 | Volpenhein |
| 4,402,907 A | 9/1983 | Clark |
| 4,636,322 A | 1/1987 | Nalesnik et al. |
| 4,729,791 A | 3/1988 | Laura et al. |
| 4,971,724 A | 11/1990 | Kalota |
| 5,055,230 A | 10/1991 | Clubley et al. |
| 5,142,072 A | 8/1992 | Stipp et al. |
| 5,209,861 A | 5/1993 | Gschwender et al. |
| 5,254,272 A | 10/1993 | Walters et al. |
| 5,275,744 A | 1/1994 | Ho |
| 5,484,542 A | 1/1996 | Cahoon et al. |
| 5,531,934 A | 7/1996 | Freeman et al. |
| 5,611,991 A | 3/1997 | Naraghi et al. |
| 5,616,544 A | 4/1997 | Kalota et al. |
| 5,627,259 A | 5/1997 | Thaler et al. |
| 5,633,326 A | 5/1997 | Patil et al. |
| 5,643,859 A | 7/1997 | Gutierrez et al. |
| 5,744,069 A | 4/1998 | Maeda et al. |

(Continued)

FOREIGN PATENT DOCUMENTS

WO    WO 2005/071050 A1    8/2005

OTHER PUBLICATIONS

Lubrizol, et al., "VEG-ESTER™ GY-300 Additive Technology," Metalworking Fluid Additives, pp. 1-4, downloaded on Sep. 19, 2016.

*Primary Examiner* — Anthony J Green
(74) *Attorney, Agent, or Firm* — Fay Sharpe LLP

(57) ABSTRACT

A corrosion-inhibiting composition includes a diluent and a mixture of organic salts of half ester-half acids of a dioic acid with of a glyceride group with a fatty acyl residue. Included are organic salts of glyceride-cyclic carboxylic acid anhydride adducts.

24 Claims, 1 Drawing Sheet

(56) References Cited

U.S. PATENT DOCUMENTS

| | | |
|---|---|---|
| 5,750,070 A | 5/1998 | Tang et al. |
| 5,779,938 A | 7/1998 | Naraghi et al. |
| 5,785,896 A | 7/1998 | Rother et al. |
| 5,792,729 A | 8/1998 | Harrison et al. |
| 5,804,536 A | 9/1998 | Asao et al. |
| 5,851,965 A | 12/1998 | Harrison et al. |
| 5,853,434 A | 12/1998 | Harrison et al. |
| 5,936,041 A | 8/1999 | Diana et al. |
| 6,727,207 B2 | 4/2004 | Iso et al. |
| 7,081,542 B2 | 7/2006 | Jacobs et al. |
| 7,435,707 B2 | 10/2008 | Langer et al. |
| 8,022,021 B2 | 9/2011 | Burrington et al. |
| 2013/0029891 A1 | 1/2013 | Okazaki et al. |
| 2013/0029893 A1 | 1/2013 | Okazaki et al. |
| 2013/0072408 A1 | 3/2013 | Adams et al. |

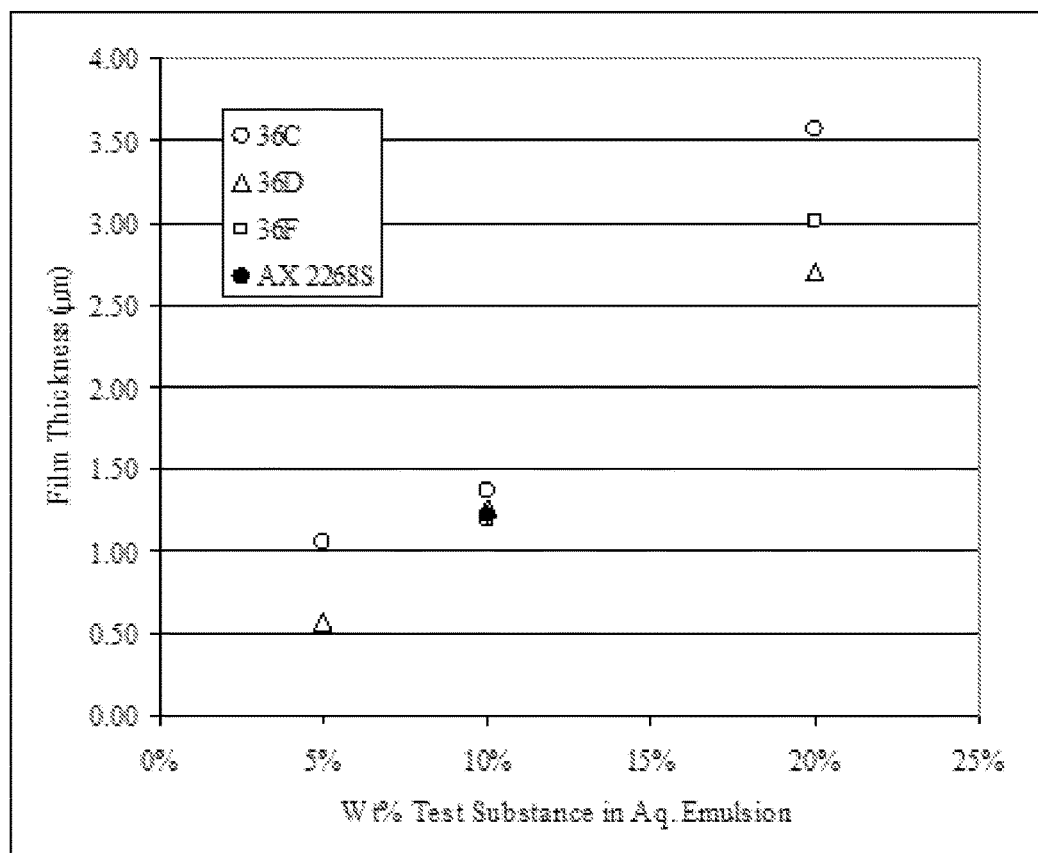

ORGANIC SALTS OF GLYCERIDE-CYCLIC CARBOXYLIC ACID ANHYDRIDE ADDUCTS AS CORROSION INHIBITORS

This application claims the benefit of PCT/US2014/068707, filed Dec. 5, 2014, and U.S. Provisional Application No. 61/913,982, filed Dec. 10, 2013, from which the PCT application claims priority, the disclosures of which are incorporated herein by reference in their entireties.

BACKGROUND

The exemplary embodiment relates to corrosion inhibitors based on organic salts of glyceride-cyclic carboxylic acid anhydride adducts and to methods of inhibiting corrosion using these corrosion inhibitors.

Corrosion inhibitors (sometimes called rust preventatives) are widely used for inhibiting atmospheric corrosion of bare metal on finished or freshly-milled metallic articles. Corrosion inhibitors in current use are often derived from petroleum waxes. These waxes are becoming scarce due to operational changes in many petroleum refineries. Petroleum-derived waxes are also considered non-renewable since they take millions of years to form. One class of corrosion inhibitors includes high-molecular weight petroleum waxes that have been partially oxidized in the presence of various metal catalysts to produce a mixture of waxy or oily organic acids. The salts of these organic acids exhibit affinity for metal surfaces, forming a hydrophobic barrier that inhibits corrosion.

It would be desirable if corrosion inhibitors that perform as well as petroleum-derived corrosion inhibitors could be derived from renewable resources, such as animal or vegetable matter.

BRIEF DESCRIPTION

In accordance with one aspect of the exemplary embodiment a corrosion inhibiting composition includes a diluent and a mixture of organic salts of half ester-half acids having the general structure of STRUCTURE (1) at a total concentration of from 0.01-30 wt. % of the composition:

STRUCTURE (1)

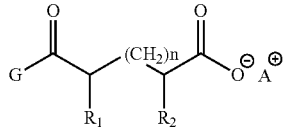

where:
n is from 0-2;
G is a glyceride residue comprising a mixture of:

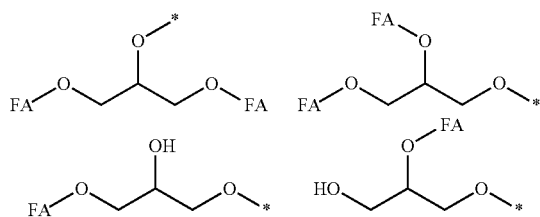

-continued

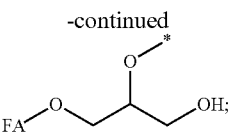

each FA is a straight-chain fatty acyl residue having from 4 to 24 carbon atoms and from 0 to 3 double bonds in the carbon chain;
$R_1$ and $R_2$ are independently selected from hydrogen, straight-chain or branched alkyl or alkenyl groups having from 1-18 (or 8-18) carbon atoms or where $R_1$ and $R_2$ together with the two carbons atoms to which they attach and the —$(CH_2)_n$— group form a cyclic structure having at least 5 carbon atoms (or 5-18 carbon atoms); and
A is a neutralizing group;
in one embodiment $R_1$ and $R_2$ may be independently selected from straight chain or branched alkyl or alkenyl groups having 8-18 carbon atoms where two ends of the carbon chain form a cyclic structure.

In accordance with another aspect of the exemplary embodiment a method for forming a corrosion inhibiting composition includes reacting a triglyceride of the general structure:

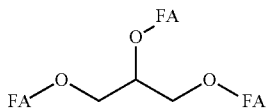

with glycerin in the presence of a transesterification catalyst to form a glyceride mixture, where each FA is a straight-chain fatty acyl residue having from 4 to 24 carbon atoms and from 0 to 3 double bonds in the carbon chain, and reacting the glyceride mixture with a cyclic carboxylic acid anhydride. The product of the reaction of the glyceride mixture with the cyclic carboxylic acid anhydride is neutralized with a neutralizing base. The neutralized reaction product is combined with a diluent to form the corrosion inhibiting composition. The neutralized reaction product is at a total concentration of from 0.01-30 wt. % of the composition.

In another embodiment, a mixture of organic salts of half ester-half acids having the general structure of STRUCTURE (1) is provided.

BRIEF DESCRIPTION OF THE DRAWING

The FIGURE shows film thickness of corrosion inhibitor films vs. emulsion treat rate.

DETAILED DESCRIPTION

Aspects of the exemplary embodiment relate to half-ester/half-acid mixtures derived from glycerides, such as renewable vegetable or animal triglycerides, that when salted with a variety of organic and inorganic bases provide corrosion inhibiting compounds that can exhibit superior performance to conventional petroleum-derived corrosion inhibitors. Also disclosed is a composition for inhibiting corrosion which incorporates the mixture of half ester-half acid organic salts, a diluent, and optionally one or more adjuvants. Also disclosed is a method of providing corrosion inhibition to a metallic substrate with the composition.

The corrosion inhibiting composition includes at least one and generally a mixture of organic salts of half ester-half acids having the general structure of STRUCTURE (1):

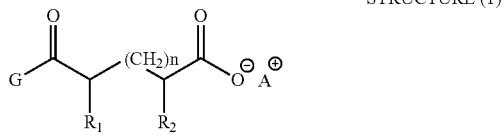

STRUCTURE (1)

where n may be from 0-2.

In particular, when n=0, the mixtures of organic salts of half ester-half acids have the general structure of STRUCTURE (2):

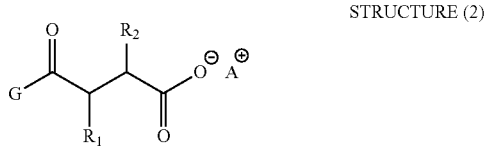

STRUCTURE (2)

where G is a glyceride residue comprising (or consisting essentially of) a mixture of:

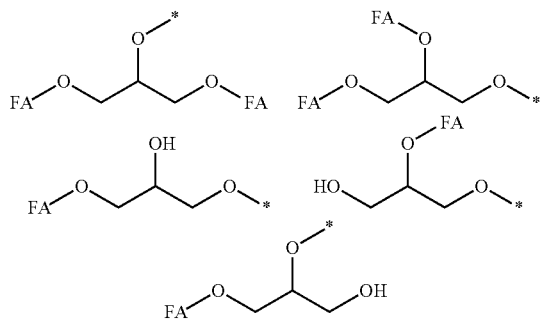

where: "- *" indicates the oxygen that attaches the glyceride residue to the rest of STRUCTURE (1) or STRUCTURE (2), each FA is a straight-chain fatty acyl residue having from 4 to 24 carbon atoms and which may have from 0 to 3 double bonds in the carbon chain, $R_1$ and $R_2$ are independently selected from hydrogen, straight-chain or branched alkyl or alkenyl groups having from 1-18 (or 8-18) carbon atoms or where $R_1$ and $R_2$ together with the two carbons atoms to which they attach and the —$(CH_2)_n$— group form a cyclic structure having at least 5 carbon atoms (or 5-18 carbon atoms); and A+ is a neutralizing group, such as a protonated organic base or a metal cation derived from a neutralizing base.

In some embodiments, the corrosion inhibiting composition described herein includes at least one and generally a mixture of organic salts of half ester-half acids having the general structure of STRUCTURE (1), as described above, where $R_1$ and $R_2$ cannot both be hydrogen when n is 0. In such embodiments at least one of $R_1$ and $R_2$ is/are independently selected from a straight-chain or branched alkyl or alkenyl group having from 1-18 carbon atoms or where $R_1$ and $R_2$ together with the two carbons atoms to which they attach and the —$(CH_2)_n$— group form a cyclic structure having at least 5 carbon atoms carbon atoms. In some embodiments at least one of $R_1$ or $R_2$ is a straight-chain or branched alkyl or alkenyl group having from 8-18 carbon atoms.

In some embodiments, the corrosion inhibiting composition described herein includes at least one and generally a mixture of organic salts of half ester-half acids having the general structure of STRUCTURE (1), as described above, where n is 0, $R_1$ and $R_2$ together form a cyclic structure that creates a 6 membered ring in the overall structure, and which may further include one or more alkyl substituent groups linked to the ring, or which may be free of any further substituent group. In some embodiments the structure includes a single alkyl substituent group, and in some of these embodiments that alkyl substituent group may be a methyl group. In such embodiments the described corrosion inhibiting composition includes at least one and generally a mixture of organic salts of half ester-half acids having the general structure of STRUCTURE (1A) and/or STRUCTURE (1B):

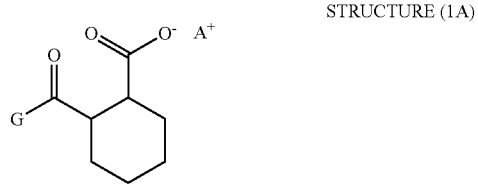

STRUCTURE (1A)

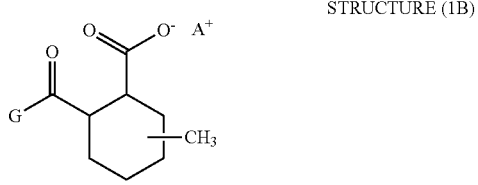

STRUCTURE (1B)

where: G is a glyceride residue comprising (or consisting essentially of) a mixture of:

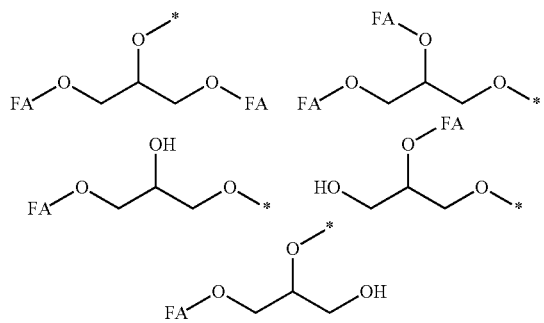

where: each FA is a straight-chain fatty acyl residue having from 4 to 24 carbon atoms and which may have from 0 to 3 double bonds in the carbon chain; and A+ is a neutralizing group, such as a protonated organic base or a metal cation derived from a neutralizing base.

By "consisting essentially of," it is meant that compounds containing residues other than G (e.g., derived from triglyceride and/or glycerol) account for less than 10 wt. % of the mixture.

The exemplary compounds are monomers, where there is only one glyceride residue per molecule and only one acid group per molecule, although small amounts of dimers and higher polymers (e.g., in total, less than 20%, or less than 10%, or less than 2% by weight of the mixture) may be present. An average molecular weight of the organic salts of STRUCTURE (1) and/or (2) in the mixture may be up to 1250 g/mole.

The glyceride G may be derived from renewable vegetable or animal triglycerides.

The fatty acyl resides FA may contain a range of carbon chain lengths, which maybe predominantly (e.g., at least 50% or at least 60%, or at least 70%) even-numbered, e.g., ranging from $C_4$ to $C_{24}$. In one embodiment, the fatty acyl residues are predominantly (e.g., at least 50% or at least 60%, or at least 70%) in the range $C_{12}$ to $C_{24}$ or in the range $C_{16}$ to $C_{20}$. In one specific embodiment, $C_{18}$ is a major component (e.g., at least 50% or at least 60% of the FA are $C_{18}$). In one embodiment, a proportion of fatty acyl resides having 3 double bonds (such as linolenic acid) is less than 50%, such as less than 20% or less than 10%. For some applications, high degrees of unsaturation, i.e., glycerides having a high proportion of polyunsaturated fatty acid residues such as linolenic acid are undesirable, owing to the higher oxidative instability that may result.

The fatty acyl residues have the general formula O—C(O)—$R_5$ where $R_5$ is a carbon chain having a number of carbon atoms predominantly in the range $C_{11}$ to $C_{23}$, e.g., predominantly in the range $C_{15}$ to $C_{19}$. Example fatty acids from which the fatty acyl residues may be derived include saturated fatty acids, such as hexanoic, heptanoic, octanoic, nonanoic, decanoic, undecanoic, tridecanoic, tetradecanoic, pentadecanoic, hexadecanoic, heptadecanoic, octadecanoic, nonadecanoic, eicosanoic, heneicosanoic, deocosanoic, tricosanoic, tetracosanoic, pentacosanoic, hexacosanoic, heptacosanoic, octacosanoic, and nonacosanoic acids, and unsaturated fatty acids, having at least one double bond, such as myristoleic, palmitoleic, sapienic, oleic, elaidic, vaccenic, linoleic, linoelaidic, α-linolenic, arachidonic, eicosapentaenoic, erucic, and docosahexaenoic acids, combinations thereof, and the like.

In one embodiment, an average number of FA groups per glyceride residue G in the mixture is at least 1 or at least 1.2, or at least 1.4.

In one embodiment the neutralizing group A+ is a protonated organic base. Example protonated organic bases include nitrogen-containing bases, such as protonated amines, alkylamines, alkanolamines, imidazoles, alkylimidazoles, and the like.

In another embodiment, the neutralizing group A+ is a metal ion such as a group I or Group II metal, such as sodium, potassium, calcium, barium, combination thereof, or the like.

In the compounds of STRUCTURE(1) or (2), the negatively charged carboxylate group is attracted to a metal surface while the rest of the molecule is very hydrophobic and repels water to retard corrosion significantly.

The groups FA, $R_1$, $R_2$, and A in STRUCTURE (1) or (2) may be selected to provide organic salts of glyceride-cyclic carboxylic acid anhydride adducts which give significantly improved rust prevention as compared to traditional corrosion inhibitory compounds based on partial oxidation of petroleum waxes.

The mixture of organic salts of half ester-half acids according to STRUCTURES (1) and (2) may be solid or liquid at ambient temperature (25° C.). In one embodiment, the salt mixture is a liquid having a kinematic viscosity of less than 5000 mPa·s, such as less than 1000 mPa·s at 40° C., as measured according to ASTM D455. In some embodiments, the salt mixture may have a pour point, as measured according to ASTM D97-12, of 20° C. or less, such as 10° C. or less.

Method of Preparation of the Compounds of STRUCTURE (1) or (2)

The exemplary half ester-half acid salts can be produced by a method which includes three sequential steps as follows:

First, a glyceride mixture is formed by reacting a triglyceride of the general structure:

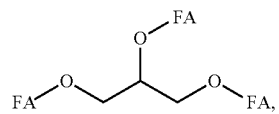

where FA is defined as above, with glycerin in the presence of a transesterification catalyst.

In a second step, the glyceride mixture is reacted with a cyclic carboxylic acid anhydride having the structure general structure of STRUCTURE (3):

STRUCTURE (3)

where $R_1$ and $R_2$ are as defined above.

The product of this reaction is a half ester-half acid having the structure of STRUCTURE (4):

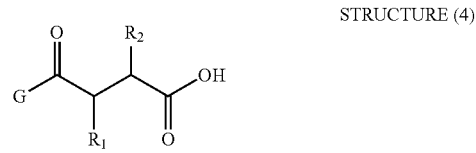

STRUCTURE (4)

where G is a glyceride residue as defined above, and $R_1$ and $R_2$ are as defined previously.

To form compounds of STRUCTURE (1) where n is 1 or more, a cyclic carboxylic acid anhydride with a 6 or 7 membered ring is used in place of STRUCTURE (3).

A third step involves neutralizing the reaction product of the second step (the half ester-half acid) with an organic base or other neutralizing base. Further details of the three steps are now provided.

1. Preparation of Glyceride Mixture

Examples of methods for preparing glyceride mixtures suitable for use herein are provided in U.S. Pat. Nos. 4,263,216 and 7,081,542.

In one embodiment, the preparation involves transesterification of a triglyceride with glycerin in the presence of an alkyltin transesterification catalyst at elevated temperatures.

The resulting glyceride mixture contains the following species, in addition to unreacted triglyceride and glycerin:

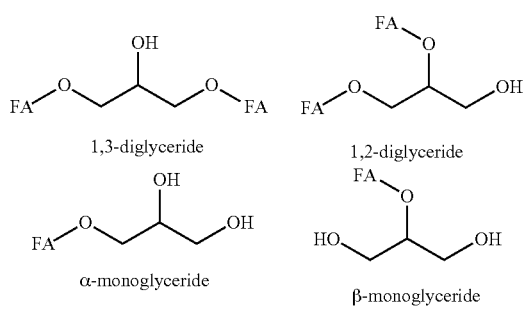

where each FA is a fatty acyl residue from the starting triglyceride, as described above.

Examples of suitable triglycerides useful herein include vegetable and animal-derived triglycerides, such as those contained in almond oil, canola oil, cocoa butter, cocoa oil, coconut oil, corn oil, cottonseed oil, flax seed oil, linseed oil, neem oil, olive oil, palm oil, palm kernel oil, palm stearin, palm butter, peanut oil, rapeseed oil, rice bran oil, safflower oil, sesame oil, soybean oil, sunflower seed oil, and tung oil, and animal-derived triglycerides such as beef tallow, butter oil, butterfat, cod liver oil, herring/fish oil, lanolin oil, lard, mutton tallow, neatsfoot oil, and sardine oil. Partially or totally hydrogenated derivatives of these oils and fats may also be employed in order to make higher-melting, waxier analogs. In one embodiment, the vegetable oil is an unhydrogenated vegetable oil and/or has less than 20 wt. % saturated fatty acids. Synthetically-produced triglycerides are also contemplated.

Example fatty acyl groups FA in such triglycerides may include, among others, those which correspond to unsaturated fatty acids, such as myristoleic acid, palmitoleic acid, sapienic acid, oleic acid, elaidic acid, vaccenic acid, linoleic acid, linoelaidic acid, α-linolenic acid, arachidonic acid, eicosapentaenoic acid, erucic acid, and docosahexaenoic acid, and saturated fatty acids, such as caprylic acid; capric acid; lauric acid, myristic acid, palmitic acid; stearic acid, arachidic acid, behenic acid, lignoceric acid, cerotic acid, isostearic acid, gadoleic acid, and combinations thereof.

As an example, the major unsaturated fatty acids in soybean oil triglycerides are approximately: alpha-linolenic acid (7-10%), linoleic acid (51%), and oleic acid (23%). It also contains the saturated fatty acids, stearic acid (4%), and palmitic acid (10%).

The second reactant used in the preparation of the glyceride mixture is glycerin. The glycerin may be natural or synthetically derived, and the purity need not be high as long as the glycerin is not significantly contaminated with water. A suitable water content of the glycerin is 0.2 wt. % or less.

The molar ratio of triglyceride to glycerin may vary, depending on the desired average number of fatty acyl groups per molecule in the final product. Molar ratios of triglyceride to glycerin from about 3:1 to about 1:2 are exemplary, with a molar ratio of 2.5:1 to 1:1, e.g., about 2:1, being suited to providing a mixture with relatively low amounts of residual triglyceride. At all ratios, some unreacted triglyceride and/or glycerin will invariably be present at the end of the transesterification reaction. These unreacted materials are generally undesirable impurities that may adversely impact the performance of the final products if their amounts are too high. The amount of unreacted triglyceride in the glyceride mixture increases as the molar ratio of triglyceride to glycerin increases. Conversely, the amount of unreacted glycerin in the glyceride mixture increases as the ratio of triglyceride to glycerin decreases.

A transesterification catalyst may be employed in order to accelerate the reaction between the triglyceride and glycerin and/or allow a lower temperature to be employed. Transesterification catalysts are well known and many are commercially available. Examples include acids (e.g., sulfuric acid, phosphoric acid, sulfonic acids), bases (e.g., alkali metal and alkaline earth metal oxides and hydroxides such as potassium hydroxide, lithium hydroxide), dry sodium or potassium salts of alcohols (sodium or potassium alkoxides), organotin compounds, and titanium compounds. Example organotin catalysts include tetrabutyltin, trioctyltin ethoxide, dibutyltin dimethoxide, dibutyltin dihydride, dibutyltin bis (2-ethylhexanoate), dibutyltin maleate, bis(tributyltin) oxide, bis(dibutylmethoxytin) oxide, and dibutyl tin dilaurate. Organic tin catalysts are available, for example, from PMC Organometallix under the trade name Fascat®, such as butyltin tris(2-ethylhexanoate), available as Fascat® 4102, dibutyltin dilaurate, available as Fascat® 4202, as well as tin(II) bis(2-ethylhexanoate), butylstannoic acid, and dibutyltin oxide. Example organic titanate catalysts are commercially available from Dorf Ketal under the trade name Tyzor®. These include tetraethyl titanate, tetraisopropyl titanate, tetra-n-propyl titanate, tetra-n-butyl titanate, tetra-2-ethylhexyl titanate, titanium acetylacetonate, and the like. In the case of sodium or potassium hydroxide catalysts, dehydration of the reaction mixture is usually required. Litharge (a lead oxide) has also been widely used as a catalyst. In one embodiment, the transesterification catalyst includes an alkyltin compound, such as dibutyltin dilaurate.

The level of the transesterification catalyst can be from about 0.001 to 0.2 wt. % of the total reactant mixture, such as at least 0.01 wt. %.

The reaction temperature and reaction time in this step of the process may be suitably selected such that the reactants fully equilibrate to form the thermodynamically stable glyceride mixture. As an example, the transesterification reaction can be performed by reacting the triglyceride with the glycerin for a period of about 2-16 hours at a temperature of about 180° C. The triglyceride and glycerin may be combined as liquids (the triglyceride being pre-melted if it is a solid at room temperature), and heated to about 180° C. with continuous agitation. The catalyst may be added after the reactants are up to temperature. Heating at about 180° C. is continued for about 8 hours, during which time the separate glycerin phase disappears. A blanket of nitrogen or other inert gas can be maintained over the reaction mixture throughout the process in order to prevent trace oxidation of the glyceride mixture resulting in higher color.

The fatty acyl residues tend to reach their natural equilibrium distribution on the various available alcohol sites in the reaction mixture. The resulting equilibrium mixture is generally not a statistically random distribution of the fatty acyl groups on the glycerin oxygen atoms because thermodynamically the acyl groups preferentially locate on the two primary glycerin oxygen atoms rather than the central secondary oxygen. The fatty acyl residues thus predominantly reside on the primary alcohol sites. Thus the α-monoglyceride and 1,3-diglyceride tend to have significantly higher concentrations in the thermodynamically stable glyceride mixture than would be expected based on a statistically random distribution. For example, it has been observed that in a mixture that has on average two fatty acyl groups per glycerin, the proportion of 1,3-diglyceride may be as high as 80% or more if the mixture is fully equilibrated in the presence of a transesterification catalyst, whereas the statistically calculated molar percentage of 1,3-diglyceride in a completely random mixture is only about 15% (see, for example, U.S. Pat. No. 4,263,216).

The glyceride mixture thus obtained is cooled from the reaction temperature and may be used directly without purification. Knowing the average molecular weight of the starting triglyceride (for example by calculation from the saponification value), the average molecular weight per free hydroxyl group in the glyceride mixture may be readily calculated. This calculated weight per hydroxyl may be used when determining the molar ratio of reactants for the next step of the process.

The exemplary glyceride mixture thus obtained has from about 0.75 to about 2.0 free hydroxyl groups, on average, per molecule, with an average of 1.0 being particularly suitable.

2. Reaction of Glyceride Mixture with Cyclic Carboxylic Acid Anhydride

The second step involves the reaction between a glyceride mixture, as described above, and a cyclic carboxylic acid anhydride having the general structure:

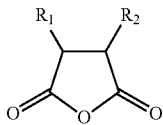

where $R_1$ and $R_2$ are independently selected from: hydrogen; straight-chain or branched alkyl groups having from 1-18 carbon atoms each or together (e.g., together with the carbon atoms to which they are attached) form a cyclic structure including a ring containing at least 5 carbon atoms. Specific examples of these cyclic carboxylic acid anhydrides include succinic anhydride, hexahydrophthalic anhydride (HHPA), methylhexahydrophthalic anhydride (MHHPA), octenylsuccinic anhydride (OSA), octadecenylsuccinic anhydride (ODSA), and combinations thereof.

In one embodiment, at least one of $R_1$ and $R_2$ is not H. In one embodiment, $R_1$ and $R_2$ form a cyclic structure, as in hexahydrophthalic anhydride and methylhexahydrophthalic anhydride. In one embodiment, where $R_1$ and $R_2$ form a cyclic structure, the ring formed is saturated.

While five-membered ring cyclic anhydrides are more economical than six-membered and larger cyclic anhydrides, it is also contemplated that anhydrides having additional carbon atoms in the anhydride ring may be employed.

Although maleic anhydride and phthalic anhydride may be employed in this step of the process, these cyclic carboxylic acid anhydrides may be undesirable due to toxicity concerns. Fine filamentous crystals of these specific anhydrides can also form in the vapor space of the reaction vessel. In the case of maleic anhydride, the carbon-carbon double bond may also be undesirable in the final product.

In one embodiment, a mixture of two or more cyclic anhydrides is employed to impart different properties to the corrosion inhibitor. The smallest, most flexible anhydride is succinic anhydride. HHPA and MHHPA introduce rigidity near the acid group because of the ring structure. Alkenyl succinic anhydrides, such as OSA and ODSA, introduce a third fatty tail, the length of which can be the same as or different from the length of the two tails from the glyceride.

An exemplary molar ratio of the cyclic carboxylic acid anhydride to the free hydroxyl groups in the glyceride mixture is from 0.8 to 1.0, such as a ratio of about 0.9.

The cyclic carboxylic acid anhydride is suitably added to the glyceride mixture at the about lowest temperature at which the glyceride mixture is completely melted. The mixture of the two reagents is then heated to a sufficient temperature and for sufficient time such that substantially complete reaction between the cyclic anhydride and free hydroxyl groups of the glyceride mixture occurs. A final reaction temperature of about 120-130° C. is generally sufficient for most cyclic anhydrides. At these reaction temperatures, the reaction is usually substantially complete after about four to five hours, however longer reaction times may be employed in some cases. No catalyst is required for this reaction. The cyclic anhydride is thus converted into a half acid/half ester type structure of the form shown in STRUCTURE (4) in which the glyceride residue G is connected through one of the oxygen atoms that was a free OH group in the glyceride mixture above.

During this reaction the removal of water from the reaction mixture is generally to be avoided. Water removal can be avoided using a condenser to return water vapor to the reaction and/or by water addition. If water is removed, this indicates that a second esterification is occurring between the free carboxylic acid in the structure above and a free hydroxyl group of the glyceride mixture. This is an undesired reaction that produces a di-ester having the structure:

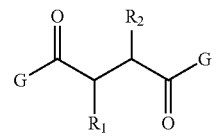

where G is defined as above.

In one embodiment, the reaction between the glyceride mixture and the cyclic carboxylic acid anhydride is monitored by periodic measurement of the acid number of the reaction mixture (i.e., milligrams of KOH required to titrate one gram of the reaction mixture to a neutral pH). Initially, each mole of cyclic carboxylic acid anhydride in the reaction mixture may be considered as two moles of acid. The glyceride mixture contributes negligible acidity. Theoretically, the acid number of the reaction mixture should fall to exactly one half of this initial calculated value if all of the cyclic carboxylic acid anhydride reacts as desired. In practice, the acid number rarely reaches more than about 90-95% of this theoretical value, at which point the reaction can be deemed to be substantially complete. In another embodiment, the reaction is monitored by infrared spectroscopy. The cyclic carboxylic acid anhydrides exhibit strong characteristic twin absorbance bands at about 1860 and 1775 cm−1. These bands continuously diminish as the reaction progresses.

This reaction can be conducted by combining the glyceride mixture and cyclic carboxylic acid anhydride at a temperature at which the glyceride is liquid and then slowly warming the mixture to a temperature of 120 to 140° C. for a period of about 4-8 hours, while ensuring that that water is not allowed to distill from the reaction mixture during this time. In this step, a molar ratio of cyclic carboxylic acid anhydride to free hydroxyl groups in the glyceride mixture can be from about 0.8:1 to about 1.0:1.

3. Neutralization of Glyceride/Cyclic Carboxylic Acid Anhydride Adducts

The half acid/half ester adduct resulting from the reaction between a glyceride mixture and a cyclic carboxylic acid anhydride produced in step 2 is neutralized with an organic or inorganic base to produce the mixture of STRUCTURE (1) or (2). Organic bases useful for this step include compounds containing a combination of the elements carbon, hydrogen, nitrogen, oxygen, sulfur, and/or phosphorus and having sufficient basicity such that the base deprotonates the carboxylic acid residue of the half acid/half ester adduct.

The neutralization reaction may be conducted at a relatively low temperature, but warm enough such that the half ester-half acid mixture is liquid. The neutralization reaction is exothermic, so in general, no additional heating of the reactants is required in this step. For solid bases such as imidazole, however, mild heating may beneficially accelerate the neutralization process by increasing the rate of dissolution of the solid base into the reaction mixture. In this step, a molar ratio of organic base to the acid groups in the half acid/half ester adducts can be about 0.8 to 1.2, such as a ratio of about 0.9 to 1.1, or about 0.9 to 1.0. Excess organic base can result in increased odor in the final product if the base is an odoriferous volatile amine.

Representative organic bases include primary, secondary, and tertiary amines and diamines. Exemplary amines may have linear, branched, or cyclic alkyl groups. The number of carbons in the alkyl groups can be from 1 to about 18. Other organic bases include nitrogen-containing heterocycles such as imidazole and alkyl-substituted imidazoles; pyridine or substituted pyridines; morpholine, piperazine, piperidine, and their substituted derivatives; alkanolamines and alkyl-alkanolamines; ether amines, combinations thereof, and the like.

Examples of organic bases useful for the neutralization step include: primary alkylamines, such as methylamine, ethylamine, n-propylamine, n-butylamine, n-hexylamine, n-octylamine, 2-ethylhexylamine, benzylamine, 2-phenyl-ethylamine, cocoamine, oleylamine, and tridecylamine (CAS#86089-17-0); secondary and tertiary alkylamines such as isopropylamine, sec-butylamine, tert-butylamine, and tributylamine, cyclopentylamine, cyclohexylamine, and 1-phenylethylamine; dialkylamines, such as dimethylamine, diethylamine, dipropylamine, diisopropylamine, dibutylamine, dicyclohexylamine, di-(2-ethyhexyl)amine, dihexylamine, ethylbutylamine, N-ethylcyclohexylamine, and N-methylcyclohexylamine; cycloalkylamines, such as piperidine, N-methylpiperidine, N-ethylpiperidine, pyrrolidine, N-methylpyrrolidine, and N-ethylpyrrolidine; aliphatic alicylclic and aromatic diamines, such as 3-dimethylamino-1-propylamine; alkanolamines such as 2-aminoethanol (monoethanolamine), diethanolamine, triethanolamine, monoisopropanolamine, diisopropanolamine, triisopropanolamine, 2-(2-aminoethoxy)ethanol, 5-aminopentanol, 3-aminopropanol, 2-amino-2-methylpropanol, 2-dimethylamino-2-methylpropanol, 2-amino-2-methyl-1,3-propanediol, 2-amino-2-ethyl-1,3-propanediol, 2-amino-2-hydroxymethyl-1,3-propanediol, morpholine, and N-(2-hydroxyethyl)morpholine; alkylalkanolamines such as N-methylethanolamine, N-methyldiethanolamine, N-ethyldiethanolamine, N,N-dimethylethanolamine, N,N-diethylethanolamine, N-butylethanolamine, N-butyldiethanolamine, N-octylethanolamine, and N-octyldiethanolamine; heterocycles such as imidazole, 1-methylimidazole, 2-methylimidazole, 1-ethylimidazole, 2-ethylimidazole, pyridine, 2-methylpyridine, 3-methylpyridine, 4-methylpyridine; quaternary ammonium hydroxides such as tetramethylammonium hydroxide, tetraethylammonium hydroxide, and tetrabutylammonium hydroxide; ether amines, such as 3-(isotridecyloxy)propylamine; and polyfunctional materials such as guanidine, tetramethylguanidine, 1,8-diazabicyclo[5.4.0]undec-7-ene, 1,5-diazabicyclo[4.3.0]non-5-ene, tert-butylimino-tris(dimethylamino)phosphorane; combinations thereof, and the like.

Inorganic neutralizing bases include ammonia and oxides and hydroxides of Group I and II metals, such as sodium hydroxide and calcium oxide (lime). The neutralizing base may be selected to provide desirable solubility in the selected diluent. By way of example, a hydrophobic amine, such as 2-ethylhexylamine, may be selected to provide a salt that is soluble in an organic solvent. A water soluble amine, such as 3-amino-1-propanol, may be selected to provide a salt that is water emulsifiable. Calcium oxide or hydroxide may be selected to provide an oil-soluble and/or solvent-soluble, thixotropic composition.

The resultant salts are suitably homogeneous materials when molten, and may be liquids at room temperature. Slurries, gels, partial solids, and two-phase liquids are generally undesirable physical forms for the salt products for some applications due to the difficulty in applying a uniform amount of these types of materials.

An example preparation scheme is shown in Scheme 1:

Scheme 1

Step 1: React vegetable oil with glycerin

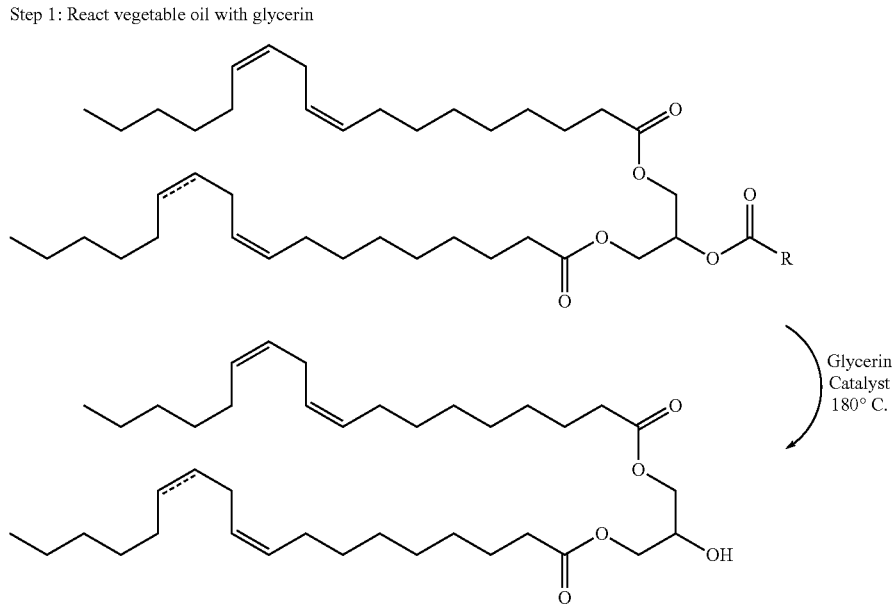

Step 2: React diglyceride with anhydride

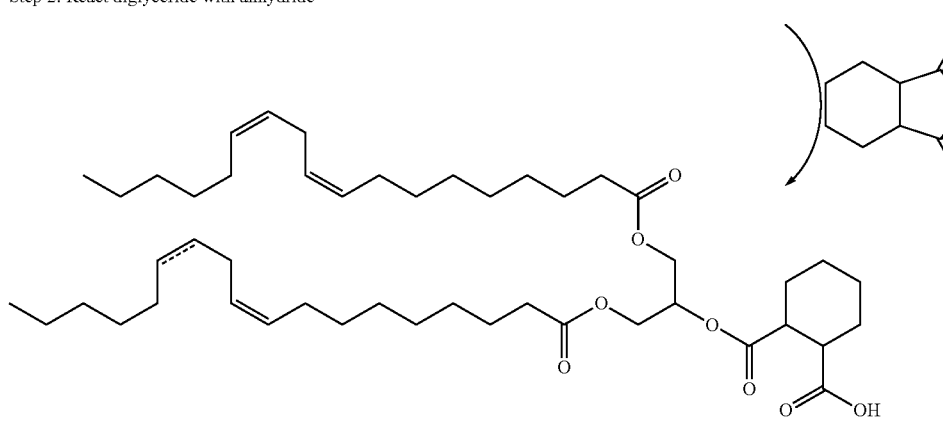

Step 3: Neutralize free acid

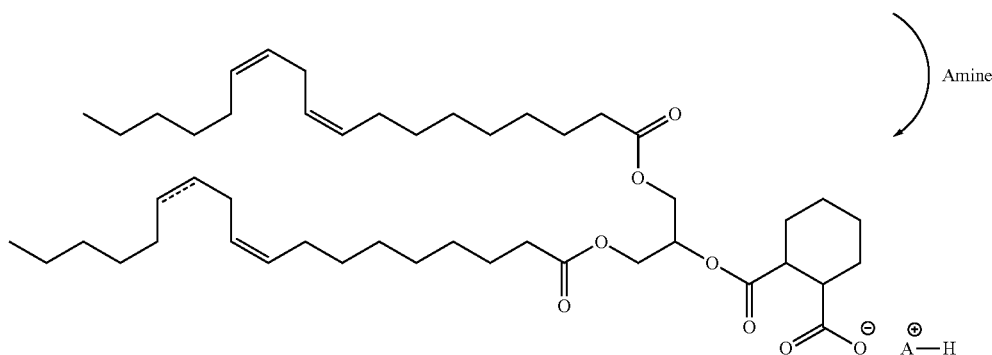

Here, R can be the same as the other fatty acid groups or a different fatty acid group. Exemplary amines and other organic bases which can be used in the neutralization are described above. As will be appreciated, in the case of an inorganic base, the neutralization can be carried out by reacting the mixture of anhydride-capped mono- and diglycerides with an aqueous solution of ammonia or a metal hydroxide, such as sodium or calcium hydroxide.

Corrosion Inhibiting Composition

An organic salt of a glyceride-cyclic carboxylic acid anhydride adduct as described above can be utilized as a corrosion inhibitor in a corrosion inhibiting composition. The corrosion inhibiting composition may include from 0.01-30 wt. % of the mixture of organic salts of half ester-half acids according to STRUCTURE (1) or (2). In various embodiments, the corrosion inhibiting composition includes at least 0.25 wt. % or at least 1 wt. % of the mixture of organic salts according to STRUCTURE (1) or (2), and in some embodiments, up to 25 wt. %, or up to 10 wt. %, or up to 5 wt. %.

The composition further includes at least one diluent in which the exemplary mixture of salts is substantially dispersed or dissolved. The diluent is a generally a liquid with a viscosity of less than 500 mPa·s or less than 150 mPa·s, at ambient temperature (25° C.). The diluent may be selected from organic solvents, petroleum and vegetable oils, water, and combinations thereof. The diluent may be present in the corrosion inhibiting composition at a total concentration of at least 10 wt. %, such as at least 20 wt. %, or at least 50 wt. %, or at least 70 wt. % and in one embodiment, up to 99.99 wt. %, or up to 99.75 wt. %, or up to 99 wt. % diluent. In some embodiments, the corrosion inhibiting composition is in the form of an oil-in-water or water-in-oil emulsion.

The composition may further include one or more adjuvants selected from natural and synthetic waxes, fatty acids, normal and overbased detergents, such as metal sulfonates, other corrosion inhibitors, surfactants, demulsifiers, defoamers, biocidal agents, viscosity modifiers, pigments, and the like.

Example Diluents

Example liquid diluents suitable for use in the corrosion inhibiting composition include water, volatile organic solvents, and oils of lubricating viscosity. In general, the diluent may serve as a carrier solvent and/or as the continuous phase of an emulsion.

Exemplary volatile organic solvents include alcohols, glycols, toluene, aromatic solvents, terpenoids, terpenes, esters, ethers, acetals, polar aprotic solvents, ketones, and derivatives and combinations thereof. Examples include aromatics, such as xylene, toluene, benzene, and halogenated derivatives, such as chlorobenzene; esters such as ethyl acetate, n-butyl acetate, isobutyl acetate, methylglycol acetate, ethylglycol acetate, methoxypropyl acetate, 2,2,4-trimethyl-1,3-pentanediol monoisobutyrate, dipropylene glycol monomethyl ether acetate, propylene glycol monoethyl ether acetate, propylene glycol monomethyl ether acetate, ethylene carbonate, methyl acetate, ethyl lactate, methyl formate; ethers such as butyl glycol, tetrahydrofuran, dioxane, ethylglycol ether, diethylene glycol monoethyl ether, diethylene glycol monomethyl ether, diethylene glycol mono-n-butyl ether, diethylene glycol mono-n-hexyl ether, diethylene glycol diethyl ether, diethylene glycol dimethyl ether, diethylene glycol di-n-butyl ether, diethylene glycol di-n-hexyl ether, ethylene glycol bis-2-ethylhexyl ether, ethylene glycol di-n-butyl ether, ethylene glycol di-n-hexyl ether, ethylene glycol di-n-propyl ether, dipropylene glycol dimethyl ether, dipropylene glycol monomethyl ether, dipropylene glycol mono-n-butyl ether, dipropylene glycol mono-n-propyl ether, dipropylene glycol mono-tert-butyl ether, dipropylene glycol di-tert-butyl ether, propylene glycol monoethyl ether, propylene glycol monomethyl ether, propylene glycol mono-n-propyl ether, propylene glycol monophenyl ether, propylene glycol mono-tert-butyl ether, propylene glycol diphenyl ether, propylene glycol mono-n-butyl ether, tripropylene glycol monomethyl ether, and poly (allyl glycidyl ether); ketones such methyl ethyl ketone; alcohols and glycols, such as methanol, ethanol, isopropanol (IPA), propanol, butanol, isobutanol, tert-butanol, ethylene glycol, diethylene glycol, propylene glycol, 1,3-propanediol, butanediol, benzyl alcohol, glycerine; polar aprotic solvents such as dimethylformamide, DMPU (dimethyl pyrimidinone), DMSO (dimethyl sulfoxide), dimethylacetamide, N-methylpyrrolidone, dimethyl acetamide, tetrahydrofuran, acetonitrile, acetone; acetals, such as dimethoxymethane, dibutoxymethane, glycerol formal, diethoxymethane; halogenated solvents, such as methylene chloride and trichloromonofluoroethane; dibutyl phthalate, tris(butoxyethyl) phosphate, low-boiling naptha (liquid hydrocarbon mixtures with a boiling point between 30° C. and 90° C.), and mineral spirits (a mixture of predominantly aliphatic and alicyclic C6 to C12 hydrocarbons, with a maximum content of 25% of C7 to C12 aromatic hydrocarbons and a boiling point typically between 60° C. and 70° C.).

In general, the volatile organic solvent can be any compound that is formed from the elements carbon and hydrogen, with optionally one or more of oxygen, nitrogen, halogen and phosphorus (excluding the exemplary salt mixture, carbon monoxide, carbon dioxide, carbonic acid, and ammonium carbonate). The volatile organic solvent is generally a compound in which the salt is soluble, when present in at least the lowest concentrations disclosed herein. The volatile organic solvent can have a boiling point of up to 250° C. when measured at a standard atmospheric pressure of 101.3 kPa.

The volatile organic solvent(s) may be present in the corrosion-inhibiting composition at from 0.1 to 99.9 wt. %, e.g., 50 to 99.9 wt. %, or 90 to 99.5 wt. % or 95 to 99.5 wt. %.

Oils useful herein include naphthenic and paraffinic mineral oils, which may be refined or unrefined. Unrefined oils are those obtained directly from a natural or synthetic source without further purification. For example, a shale oil obtained directly from retorting operations, a petroleum oil obtained directly from distillation or ester oil obtained directly from an esterification process and used without further treatment would be an unrefined oil. Refined oils are similar to the unrefined oils except that they have been further treated in one or more purification steps to improve one or more properties. Purification techniques include solvent extraction, acid or base extraction, filtration, percolation, or similar purification techniques. Exemplary synthetic lubricating oils include hydrocarbon oils such as polymerized and interpolymerized olefins (e.g., polybutylenes, polypropylenes, propylene-isobutylene copolymers, poly(1-hexenes, poly(1-octenes), poly(1-decenes), and mixtures thereof); alkylbenzenes (e.g., dodecylbenzenes, tetradecylbenzenes, dinonylbenzenes, and di(2-ethylhexyl)-benzenes); polyphenyls (e.g., biphenyls, terphenyls, and alkylated polyphenyls), alkylated diphenyl ethers and alkylated diphenyl sulfides and the derivatives, analogs, and homologs thereof.

Other suitable oils are natural oils such as animal oils and plant oils, such as castor oil, cottonseed oil, rapeseed oil, soybean oil, and lard oil.

The diluent may be present at a total concentration of 0.1-99.9 wt. % of the corrosion-inhibiting composition. In one embodiment, the lubricating oil is present at up to 60 wt. % of the corrosion-inhibiting composition, e.g., at least 5 wt. %.

The examples below suggest that for good protection against corrosion, suitable carrier solvents are generally those that evaporate completely within a short time, such as solvents with a boiling point of below 150° C.

Example Adjuvants

Exemplary adjuvants which may be present in the corrosion-inhibiting composition include natural and synthetic waxes, fatty acids, normal and overbased detergents, such as metal sulfonates, demulsifiers, other corrosion-inhibiting compounds, biocidal agents, surfactants, and the like.

Example waxes include petroleum, synthetic, and natural waxes, oxidized waxes, microcrystalline waxes, wool grease (lanolin) and other waxy esters, and mixtures thereof. Petroleum waxes are paraffinic compounds isolated from crude oil via some refining process, such as slack wax and paraffin wax. Synthetic waxes are waxes derived from petrochemicals, such as ethylene or propylene. Synthetic waxes include polyethylene, polypropylene, and ethylene-propylene copolymers. Natural waxes are waxes produced by plants and/or animals or insects. These waxes include beeswax, soy wax and carnauba wax. Insect and animal waxes include beeswax, spermaceti and the like. Petrolatum and oxidized petrolatum may also be used in these compositions. Petrolatums and oxidized petrolatums may be defined, respectively, as purified mixtures of semisolid hydrocarbons derived from petroleum and their oxidation products. Microcrystalline waxes may be defined as higher melting point waxes purified from petrolatums.

The wax(es) may be present in the corrosion-inhibiting composition at from 0.1 to 75 wt. %, e.g., 0.1 to 50 wt. %.

Fatty acids useful herein include monocarboxylic acids of about 8 to about 35 carbon atoms, and in one embodiment about 16 to about 24 carbon atoms. Examples of such monocarboxylic acids include unsaturated fatty acids, such as myristoleic acid, palmitoleic acid, sapienic acid, oleic acid, elaidic acid, vaccenic acid, linoleic acid, linoelaidic acid; α-linolenic acid; arachidonic acid; eicosapentaenoic acid; erucic acid, docosahexaenoic acid; and saturated fatty acids, such as caprylic acid; capric acid; lauric acid, myristic acid; palmitic acid; stearic acid, arachidic acid, behenic acid; lignoceric acid, cerotic acid, isostearic acid, gadoleic acid, tall oil fatty acids, combinations thereof, and the like. These acids may be saturated, unsaturated, or have other functional groups, such as hydroxy groups, as in 12-hydroxy stearic acid, from the hydrocarbyl backbone. Other example carboxylic acids are described in U.S. Pat. No. 7,435,707.

The fatty acid(s) may be present in the corrosion-inhibiting composition at from 0.1-50 wt. %, e.g., 0.1 to 25 wt. %, or 0.1 to 10 wt. %.

Example overbased detergents include overbased metal sulfonates, overbased metal phenates, overbased metal salicylates, overbased metal saliginates, overbased metal carboxylates, overbased calcium sulfonate detergents and the like. The overbased detergents contain metals such as Mg, Ba, Sr, Zn, Na, Ca, K, and mixtures thereof and the like. Overbased detergents are metal salts or complexes characterized by a metal content in excess of that which would be present according to the stoichiometry of the metal and the particular acidic organic compound reacted with the metal, e.g., a sulfonic acid.

The term "metal ratio" is used herein to designate the ratio of the total chemical equivalents of the metal in the overbased material (e.g., a metal sulfonate or carboxylate) to the chemical equivalents of the metal in the product which would be expected to result in the reaction between the organic material to be overbased (e.g., sulfonic or carboxylic acid) and the metal-containing reactant used to form the detergent (e.g., calcium hydroxide, barium oxide, etc.) according to the chemical reactivity and stoichiometry of the two reactants. Thus, while in a normal calcium sulfonate, the metal ratio is one, in the overbased sulfonate, the metal ratio is 4.5.

Examples of such detergents are described, for example, in U.S. Pat. Nos. 2,616,904; 2,695,910; 2,767,164; 2,767,209; 2,798,852; 2,959,551; 3,147,232; 3,274,135; 4,729,791; 5,484,542 and 8,022,021.

The overbased detergents may be used alone or in combination. The overbased detergents may be present in the range from about 0.1 wt. % to about 20%; such as at least 1 wt. % or up to 10 wt. % of the composition.

Exemplary surfactants include nonionic polyoxyethylene surfactants such as ethoxylated alkyl phenols and ethoxylated aliphatic alcohols, polyethylene glycol esters of fatty, resin and tall oil acids and polyoxyethylene estesr of fatty acids or anionic surfactants such as linear alkyl benzene sulfonates, alkyl sulfonates, alkyl ether phosphonates, ether sulfates, sulfosuccinates, and ether carboxylates.

Demulsifiers useful herein include polyethylene glycol, polyethylene oxides, polypropylene alcohol oxides (ethylene oxide-propylene oxide) polymers, polyoxyalkylene alcohol, alkyl amines, amino alcohol, diamines or polyamines reacted sequentially with ethylene oxide or substituted ethylene oxide mixtures, trialkyl phosphates, and combinations thereof, and the like.

The demulsifier(s) may be present in the corrosion-inhibiting composition at from 0.0001 to 10 wt. %, e.g., 0.0001 to 2.5 wt. %.

Other corrosion inhibitors in addition to the exemplary compounds may also be used in the compositions provided herein. The corrosion inhibitors which may be used include thiazoles, triazoles and thiadiazoles. Examples include benzotriazole, tolyltriazole, octyltriazole, decyltriazole, dodecyltriazole, 2-mercaptobenzothiazole, 2,5-dimercapto-1,3,4-thiadiazole, 2-mercapto-5-hydrocarbylthio-1,3,4-thiadiazoles, 2-mercapto-5-hydrocarbyldithio-1,3,4-thiadiazoles, 2,5-bis(hydrocarbylthio)-1,3,4-thiadiazoles, and 2,5-bis-(hydrocarbyldithio)-1,3,4-thiadiazoles. Other suitable inhibitors of corrosion include ether amines; polyethoxylated compounds such as ethoxylated amines, ethoxylated phenols, and ethoxylated alcohols; imidazolines; and the like. Other suitable corrosion inhibitors include alkenylsuccinic acids in which the alkenyl group contains about 10 or more carbon atoms such as, for example, tetrapropenylsuccinic acid, tetradecenylsuccinic acid, hexadecenylsuccinic acid, and the like; long-chain alpha, omega-dicarboxylic acids in the molecular weight range of about 600 to about 3000; and other similar materials. Other non-limiting examples of such inhibitors may be found in U.S. Pat. Nos. 3,873,465, 3,932,303, 4,066,398, 4,402,907, 4,971,724, 5,055,230, 5,275,744, 5,531,934, 5,611,991, 5,616,544, 5,744,069, 5,750,070, 5,779,938, and 5,785,896; Corrosion Inhibitors, C. C. Nathan, ed., NACE, 1973; I. L. Rozenfeld, Corrosion Inhibitors, McGraw-Hill, 1981; Metals Handbook, 9$^{th}$ Ed., Vol. 13—Corrosion, pp. 478497; Corrosion Inhibitors for Corrosion Control, B. G. Clubley, ed., The Royal Society of Chemistry, 1990; Corrosion Inhibitors, European Federation of Corrosion Publications Number 11, The Institute of Materials, 1994; Corrosion, Vol. 2—Corrosion Control, L. L. Sheir, R. A. Jarman, and G. T. Burstein, eds., Butterworth-Heinemann, 1994, pp. 17:10-17:39; Y. I. Kuznetsov, Organic Inhibitors of Corrosion of Metals, Plenum, 1996; and in V. S. Sastri, Corrosion Inhibitors: Principles and Applications, Wiley, 1998.

The other corrosion inhibitor(s) may be present in the corrosion-inhibiting composition at from 0.0001 to 5 wt. %, e.g., 0.0001 to 3 wt. %.

Exemplary biocidal agents include dehydroacetic acid, 3-isothiazolones, sodium pyridine-2-thiol-1-oxide, 3-iodo-2-propynyl-N-n-butyl carbamate, N,N-methylenebismorpholine, (ethylenedioxy)dimethanol, 3,3-methylenebis(5-methyloxazolidine), and the like.

Dispersants which may be included in the composition include those with an oil soluble polymeric hydrocarbon backbone and having functional groups that are capable of associating with particles to be dispersed. The polymeric hydrocarbon backbone may have a weight average molecular weight ranging from about 750 to about 1500 Daltons. Exemplary functional groups include amines, alcohols, amides, and ester polar moieties which are attached to the polymer backbone, often via a bridging group. Example dispersants include Mannich dispersants, described in U.S. Pat. Nos. 3,697,574 and 3,736,357; ashless succinimide dispersants described in U.S. Pat. Nos. 4,234,435 and 4,636,322; amine dispersants described in U.S. Pat. Nos. 3,219,666, 3,565,804, and 5,633,326; Koch dispersants, described in U.S. Pat. Nos. 5,936,041, 5,643,859, and 5,627,259, and polyalkylene succinimide dispersants, described in U.S. Pat. Nos. 5,851,965, 5,853,434, and 5,792,729.

The dispersant(s) may be present in the corrosion-inhibiting composition at from 0.0001 to 50 wt. %, e.g., 1 to 25 wt. %.

The compositions disclosed herein may be used for a variety of applications, such as storage and shipping coatings, slushing oils, pickling oils, dip-tank fluids, penetrating oils, maintenance coatings, architectural, industrial, and marine coatings, and the like. In the case of longer-term coatings, such as pigmented and non-pigmented paints, primers for paint, clear coat and base coat paints, varnishes, lacquer and the like, the composition can include additives suitable for such compositions, such as one or more binders or resins, pigments, and combinations thereof.

Method of Forming the Corrosion-Inhibiting Composition

In one embodiment the composition is formed by dissolving a hydrophobic salt mixture according to STRUCTURE (1) or (2) in a volatile organic solvent at about 0.25-25 wt. % of the resulting composition, such as at least about 1 wt. %, and in one embodiment, up to 10 wt. % of the composition. Optionally, one or more adjuvants are incorporated into the composition. Exemplary organic solvents useful in this embodiment include aliphatic and aromatic hydrocarbons; glycols such as glycerine, propylene glycol, 1,3-propanediol, and ethylene glycol; alcohols such as primary alcohols (e.g., methanol, ethanol, propanol, the like, and combinations thereof), secondary alcohols (e.g., isopropanol, isobutanol, secondary butanol, the like, and combinations thereof), and tertiary alcohols (e.g., t-butanol, the like, and combinations thereof).

In some embodiments, the compounds according to STRUCTURE (1) or (2) are sparingly or fully water-soluble. Corrosion-inhibiting compositions may be suitably formulated in water or a mixture of water and one or more organic solvents, such as one or more alcohols and/or glycols.

In another embodiment the composition is formed by dissolving a hydrophobic salt mixture according to STRUCTURE (1) or (2) in a non-volatile petroleum oil, such as a paraffinic or naphthenic oil, or vegetable oil at about 0.25-25 wt. % of the resulting composition, such as at least about 1 wt. %, and in one embodiment, up to 10 wt. %, into the composition. Optionally, one or more adjuvants are incorporated into the composition.

As an example, the composition is formulated in a liquid hydrocarbon mixture having a boiling point in the range of about 30° C.-200° C., such as an aromatic naptha, e.g., heavy aromatic naptha (boiling point in the range of 90° C.-200° C.), to which one or more cosolvents, such as an alcohol or glycol may be incorporated.

In another embodiment the composition is formed by dissolving an emulsifiable salt mixture according to STRUCTURE (1) or (2) (for example, a salt formed by neutralizing a glyceride-cyclic carboxylic acid anhydride adduct with a water-soluble amine, such as triethanolamine, an alkanolamine, or an inorganic hydroxide such as NaOH) in water, at about 0.25-25 wt. % of the resulting composition, such as at least about 1 wt. %, and in one embodiment, up to 10 wt. % and an emulsion formed.

To form an emulsion, the salt mixture, solvent, water, and optionally additional adjuvants are mixed under appropriate mixing conditions to form the desired emulsion composition. The mixing may include high shear mixing, low shear mixing, or a combination thereof. The mixing may be conducted using a single mixing step or in the alternative multiple mixing steps. The mixing may be conducted on a batch basis, a continuous basis, or a combination thereof. The mixing may be conducted at a temperature in the range of about 0° C. to about 100° C., and in one embodiment about 10° C. to about 50° C., for about 1 minute to about 30 hours.

Mode of Application

The composition may be applied directly to a bare metal surface, for example, by painting, spraying, rolling, dip coating, or the like to provide a layer of about 1 μm to 1 mm in thickness. The layer may provide a self-healing effect when the layer is scratched, through evaporation and redeposition, or other mechanism.

In other embodiments the corrosion-inhibiting composition may be in the form of a paint which in addition to the compound according to STRUCTURE (1) or (2) may further include one or more of pigments or dyes, resins (alkyds, epoxies, etc.), and other components conventionally used to provide a coating which serves as a more permanent barrier to atmospheric and/or aqueous corrosion.

The metallic surfaces to be treated can be formed in whole or in part from ferrous and/or non-ferrous metals. In general, the total metal content of the body or surface of the body to be treated is at least 10 wt. % or at least 30 wt. % or at least 50 wt. %, and can be up to 99 or 100 wt. %. The metal body/surface may be a metal or metal alloy, such as iron, steel, aluminum, copper, brass, or the like where the total metal content may be at least 50 wt. % or at least 70 wt. % of the entire body or of a metallic surface layer to be protected. Suitable surfaces to be protected are those subject to atmospheric pollution, such as building materials, automobile parts, and the like, surfaces exposed to aqueous environment's such as boilers, ship components, submerged platforms, and the like, and surfaces exposed to oils and fuels, such as engines, gas and oil pipelines, and the like.

The metal part to be protected can be dipped into, sprayed with, brushed with, or otherwise coated with the resulting solution/emulsion. In the case of a composition containing a volatile solvent, the volatile organic solvent can then be evaporated from the composition film. After the volatile organic solvent has evaporated, a thin, rust preventive film of the hydrophobic salt adheres to the metal part.

In the case of compositions containing non-volatile diluents, the metal part to be protected may be dipped into, sprayed with, or otherwise coated with the solution. A thin, rust preventive film of the hydrophobic salt in combination with the non-volatile oil remains coated on the metal part.

In the case of compositions in the form of emulsions, the metal part to be protected may be dipped into, sprayed with, or otherwise coated with the emulsion. After the water has evaporated, a thin, rust preventive film of the emulsifiable salt adheres to the metal part.

In each case, a conventional paint may be subsequently applied. In another embodiment, the salt-containing film may be removed prior to further processing of the metal part. In another embodiment, the composition is in the form of a paint or other coating.

The examples below suggest that the salts disclosed herein are efficacious corrosion inhibitor compounds that can significantly delay the onset of atmospherically-induced rust on bare ferrous metal articles, such as freshly cast, milled, or worked iron or steel pieces or parts, by way of example.

EXAMPLES

The following methods can be used for preparation of organic salts of glyceride-cyclic carboxylic acid anhydride adducts.

The following reactants were employed:
Vegetable-Derived Triglycerides:

As example triglycerides, soybean oil (SYBO), rapeseed oil (RPSO), coconut oil (ONTO) (obtained from Cargill Industrial Oils and Lubricants), tallow oil (obtained from Werner G. Smith Co, Cleveland Ohio), and two partially hydrogenated derivatives of soybean oil available commercially from Cargill Industrial Oils and Lubricants under the trade names S-113 Wax and S-130 Wax (S-113 and S-130) were obtained. S-113 is a partially hydrogenated soybean oil stock wax with melting point ~113° F. (~45° C.); S-130 is a partially hydrogenated soybean oil stock wax with melting point ~130° F. (~54° C.).

These triglycerides serve to illustrate the effects of varying the degree of carbon-carbon unsaturation in the triglyceride as well as the effect of the melting point of the triglyceride.

Cyclic Carboxylic Acid Anhydrides:

The following cyclic carboxylic acid anhydrides were evaluated:

SA=succinic anhydride (dihydro-2,5-furanedione), CAS#108-30-5, obtained from Aldrich Chemical Company.)

HHPA=hexahydrophthalic anhydride (hexahydro-1,3-isobenzofurandione), CAS#85-42-7, obtained from Dixie Chemical Company.

MHHPA=methylhexahydrophthalic anhydride (hexahydromethyl-1,3-isobenzofurandione), CAS#25550-51-0, obtained from Dixie Chemical Company.

OSA=octenylsuccinic anhydride (dihydro-3-(octen-1-yl)-2,5-furandione), CAS#26680-54-6, obtained from Dixie Chemical Company.

ODSA=octadecenyl succinic anhydride, CAS#68784-12-3, obtained from Dixie Chemical Company.

Structures of these cyclic carboxylic anhydrides are as shown below:

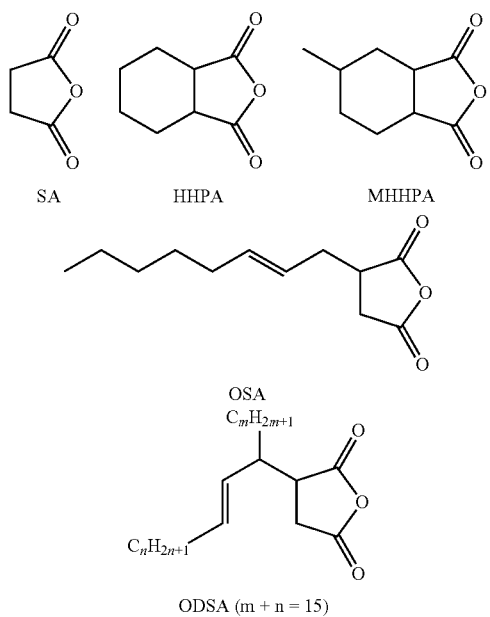

Transesterification Catalysts

As a transesterficiation catalyst, butyltin tris(2-ethylhexanoate) (BTEH), was used, which is available as Fascat® 4102 from PMC Organometallix.

Organic Bases:

The following organic bases were evaluated: 2-(2-aminoethoxy)ethanol; 5-amino-1-pentanol; 3-amino-1-propanol; 2-(2-aminoethoxy)ethanol (AEE); N,N-diethylethanolamine (DEEA); 3-dimethylamino-1-propylamine (DMAPA); N,N-dimethylethanolamine (DMEA); 2-ethylhexylamine (EHAM); imidazole; isododecyloxypropylamine, CAS#68511-40-0, obtained from Air Products Inc. under the trade name PA-16; 3-methoxypropylamine; 1-methylimidazole; 2-methylimidazole; tributylamine; triethanolamine; triisopropanolamine and Primene® 81-R—a mixture of $C_{10}$-$C_{15}$ tert-alkyl primary amines (CAS#68955-53-3), now available from Dow Chemical Co.

A. Example Preparation of Glyceride Mixtures (Step 1)

Examples 1 through 8 demonstrate the preparation of several glyceride mixtures from a variety of starting triglyceride oils using different molar ratios of triglyceride oil to glycerin in the reaction mixture.

Example 1

Soybean Oil+Glycerin 2:1 (SYBO-GLY 2:1)

Soybean Oil (1424 grams, 1.63 moles) and glycerin (75 grams, 0.814 moles) were combined in a 2-liter, 3-neck round-bottom flask equipped with a mechanical stirrer, nitrogen inlet, nitrogen outlet through a soybean oil-filled bubbler, and a heating mantle connected to a digital temperature controller. This equipment configuration is used in many of the following examples with different sized flasks. The 2-phase mixture was heated to 180° C. with agitation. BTEH (1.55 grams, 0.0026 mole) was then added to catalyze the transesterification reaction. The mixture was held at 180° C. for 8 hours with a continuous slow nitrogen sweep through the vapor space of the flask. The resultant soybean oil glyceride mixture was recovered in essentially quantitative yield as hazy yellow oil. The calculated average molecular weight of this material is 613.95 g/mole.

Example 2

Soybean Oil+Glycerin 1:1 (SYBO-GLY 1:1)

Using the same reaction apparatus as in Example 1, soybean oil (1355 grams, 1.55 mole) and glycerin (142.5 grams, 1.55 moles) were heated to 180° C. and then BTEH (2.3 grams, 0.0038 mole) was added as a catalyst. The mixture was heated at 180° C. for 11 hours under nitrogen. The product glyceride, containing an average of 1.5 fatty acid residues per molecule, was recovered in quantitative yield. Upon cooling, the product was a yellow oil that partially froze. The calculated average molecular weight of this material is 483.5 g/mole; the calculated average m.w. per OH group is 322.33.

Example 3

Soybean Oil+Glycerin 1:2 (SYBO-GLY 1:2)

Using the same reaction apparatus as in Example 1, soybean oil (1240 grams, 1.42 mole) and glycerin (260 grams, 2.82 moles) were heated to 180° C. and then BTEH (1.91 grams, 0.0032 mole) was added as a catalyst. The mixture was heated at 180° C. for 9 hours under nitrogen. The resultant product had two layers. The IR spectra of the layers were essentially identical except for the intensity of the broad OH peak at 3340 cm−1. The layers were not separated. The combined amount of the two layers represented an essentially quantitative yield. Both layers substantially froze upon cooling. The product was thoroughly re-mixed before using it to prepare subsequent derivatives. The calculated average molecular weight of this material is 353.0 g/mole; the calculated average m.w. per OH group is 176.5.

Example 4

Cargill S-113+Glycerin 2:1 (S113-GLY 2:1)

Using a 1-liter flask equipped as for Example 1, molten Cargill S-113 Wax (663 grams, 0.75 mole) and glycerin (34.6 grams, 0.376 moles) were heated to 180° C. and then BTEH (1.50 grams, 0.0025 mole) was added as a catalyst. The mixture was heated at 180° C. for a total of eight hours under nitrogen. The product glyceride mixture was recovered quantitatively. It froze to a hard wax at room temperature. The estimated average molecular weight of this material is 619.2 g/mole.

Example 5

Cargill S-130+Glycerin 2:1 (S130-GLY 2:1)

Using a 1-liter flask equipped as for Example 1, molten Cargill S-130 Wax (663 grams, 0.75 mole) and glycerin (34.5 grams, 0.375 moles) were heated to 180° C. and then BTEH (1.45 grams, 0.0024 mole) catalyst was added. The mixture was heated at 180° C. for 8 hours under nitrogen. The product glyceride mixture was recovered quantitatively.

It froze into a hard wax at room temperature. The estimated average molecular weight of this material is 621.6 g/mole.

Example 6

Tallow Oil+Glycerin 2:1 (TALLOW-GLY 2:1)

Using a 1-liter flask equipped as for Example 1, molten tallow oil (521 grams, 0.61 mole) and glycerin (28.0 grams, 0.304 mole) were heated to 180° C. and then BTEH (0.62 grams, 0.0010 mole) catalyst was added. The mixture was heated at 180° C. for 9 hours under nitrogen. The product glyceride mixture had an unpleasant odor compared to chemically-similar vegetable-based glycerides. It froze into a wax at room temperature.

Example 7

Coconut Oil+Glycerin 2:1 (ONTO-GLY 2:1)

Using a 1-liter flask equipped as for Example 1, molten Cargill Ultimate 76 Coconut Oil having a saponification number of 250.6 mg KOH/g (652 grams, 0.971 mole) and glycerin (45.0 grams, 0.489 mole) were heated to 180° C. and then BTEH (1.37 grams, 0.0023 mole) catalyst was added. The mixture was heated at 180° C. for 8 hours under nitrogen. The product glyceride mixture was hazy while molten and froze into a wax at room temperature. The calculated average molecular weight of this material is 477.6 g/mole.

Example 8

Rapeseed Oil+Glycerin 1.5:1 (RPSO-GLY 1.5:1)

Using a 2-liter flask equipped as in Example 1, rapeseed oil (1400 grams, 1.56 mole) and glycerin (96.0 grams, 1.04 mole) were heated to 180° C. and then BTEH (2.81 grams, 0.0046 mole) catalyst was added. The mixture was heated at 180° C. for 8 hours under nitrogen. The product glyceride mixture was hazy yellow oil having an acid number of 0.22 mg KOH/g. The product partially froze upon standing. The estimated average molecular weight per glyceride is 575.0 g/mole.

B. Example Cyclic Carboxylic Acid Anhydride Adducts of Glyceride Mixtures (Step 2)

Examples 9 through 26 demonstrate how the glyceride mixtures of Examples 1-8 can be further reacted with cyclic carboxylic acid anhydrides to form glyceride half-acid/half-ester adducts.

Example 9

Soybean Oil+Glycerin (2:1)+Succinic Anhydride 1:1 (SYBO-GLY-SA 2:1:3)

A glyceride mixture was prepared using soybean oil (244 grams, 0.279 mole), glycerin (13.03 grams, 0.141 moles), and BTEH (0.70 grams, 0.0012 mole), which were heated to 180° C. in a 500-mL flask equipped as in Example 1. The mixture was held at 180° C. for 6 hours under nitrogen.

After standing overnight at room temperature, the glyceride mixture was reheated to 130° C. and succinic anhydride (42.10 g, 0.420 mole) was added in a single portion, dropping the temperature to about 116° C. The temperature was re-established at 130° C. and the reaction mixture was held at this temperature until the succinic anhydride had all dissolved, resulting in a clear liquid. Fine crystals of succinic anhydride formed in the vapor space of the flask and these had to be manually knocked back down into the reaction mixture. Samples were withdrawn periodically and titrated for acid number. The acid number dropped for about five hours, and then stalled at a value of about 77-78 mg KOH/g, indicating an essentially complete reaction. The product, a soy diglyceride-succinate half-acid ester, was a clear yellow oil.

Example 10

Soybean Oil+Glycerin (2:1)+Hexahydrophthalic Anhydride 1:1 (SYBO-GLY-HHPA 2:1:3)

The glyceride mixture from Example 1 (326 g, 0.531 mole) and molten HHPA (74.0 g, 0.480 mole) were weighed directly into a tared 500-mL, 3-neck round-bottom flask. The flask was equipped as in Example 1. The mixture was heated to 120° C. and the progress of the reaction was tracked by periodic sampling for the acid number of the mixture. After 7 hours, the acid number had declined from an initial (calculated) value of 134.7 to 74.0 mg KOH/g, indicating about 90% reaction of the HHPA. The batch was cooled at this point, giving an essentially complete recovery of the soy diglyceride-hexahydrophthalate half-acid ester as a clear yellow oil.

Example 11

Soybean Oil+Glycerin (2:1)+Methylhexahydrophthalic Anhydride 1:1 (SYBO-GLY-MHHPA 2:1:3)

The glyceride product from Example 1 (320.0 g, 0.521 mole) and MHHPA (80.0 g, 0.476 mole) were combined in a 500-mL flask equipped as for Example 1. The mixture was heated to 130° C. for a period of 6 hours. The product was titrated twice for the acid number, with results of 73.8 and 72.4 mg KOH/g, indicating about 89-92% reaction of the MHHPA. The resulting soy diglyceride-methylhexahydrophthalate half-acid ester was a clear yellow oil.

Example 12

Soybean Oil+Glycerin (1:1)+Methylhexahydrophthalic Anhydride 1:1 (SYBO-GLY-MHHPA 1:1:2)

The soy glyceride mixture from Example 2, average m.w. of 483.49 (297 g, 0.614 mole) and MHHPA (103 g, 0.613 mole) were reacted together at 120° C. for a period of 5.5 hours in the same apparatus as for Example 11. The acid number stalled at 92.1 mg KOH/g, which indicates about 93% reaction of the MHHPA. The product was a viscous, clear yellow oil.

Example 13

Soybean Oil+Glycerin (1:2)+Octadecenylsuccinic Anhydride 1:1 (SYBO-GLY-ODSA 1:2:3)

The glyceride mixture of Example 3 was thoroughly re-mixed prior to weighing in order to ensure a uniform sample. The glyceride mixture (50.0 g, 0.142 mole) and ODSA (50.0 g, 0.140 mole) were combined in a glass jar and mixed by shaking. The jar was placed in an 80° C. oven for three days; an IR spectrum taken after the 3-day low-temperature cook still showed significant unreacted anhydride and the mixture was composed of two layers. The mixture was then heated on a hot plate with magnetic stirring at 130-135° C. for about 5 hours. The acid number after this second cooking was 79.8 mg KOH/g, indicating over 98% reaction of the ODSA. The product was a hazy, viscous, golden-orange liquid. The IR spectrum of the final product showed almost no anhydride.

Example 14

Cargill S-113+Glycerin (2:1)+Succinic Anhydride 1:1 (S113-GLY-SA 2:1:3)

The molten glyceride from Example 4 (201 g, 0.325 mole) and succinic anhydride (29.0 g, 0.290 mole) were combined in a 250-mL flask that was equipped as in Example 1. The slurry was heated to 120° C. for about 3 hours, during which time the succinic acid solids disappeared. The acid number dropped to 70.0 mg KOH/g, indicating 100% reaction of the succinic anhydride. The diglyceride succinate half-acid ester was a slightly hazy yellow oil when molten that froze to a white wax below about 40° C.

Example 15

Cargill S-113+Glycerin (2:1)+Hexahydrophthalic Anhydride 1:1 (S113-GLY-HHPA 2:1:3)

Molten glyceride from Example 4 (245 g, 0.369 mole) and molten HHPA (55 g, 0.357 mole) were combined at ~80° C. in a 500-mL flask that was equipped as in Example 1. The mixture was heated to 120° C. for about 4 hours. The final acid number was 71.6 mg KOH/g, indicating about 93% reaction of the HHPA. The diglyceride hexahydrophthalate half-acid ester was a clear yellow oil that froze to a soft white wax below about 40° C.

Example 16

Cargill S-113+Glycerin (2:1)+Octenylsuccinic Anhydride (S113-GLY-OSA 2:1:3)

Molten glyceride from Example 4 (229 g, 0.370 mole) and OSA (71.1 g, 0.335 mole) were combined at ~45° C. in a 500-mL flask that was equipped as described in Example 1. The mixture was heated to 120° C. for about 3.5 hours. The final acid number was 68.3 mg KOH/g, indicating about 91% reaction of the OSA. The product was a clear yellow oil while molten. It froze into a semi-solid paste upon cooling.

Example 17

Cargill S130+Glycerine (2:1)+Methylhexahydrophthalic Anhydride (S130-GLY-MHHPA 2:1:3)

The glyceride mixture from Example 5 (241 g, 0.387 mole) was melted and heated to 106° C. in a 500-mL flask equipped as for Example 1. MHHPA (59.4 g, 0.353 mole) was added in a single portion and the batch was allowed to cool to 45° C. with the heat turned off. The batch was then heated to 120° C. About 5 hours after the MHHPA was added, the acid number was 69.6 mg KOH/g, which indicates about 94% reaction of the anhydride. The product glyceride-half ester/half acid adduct was recovered quantitatively. The freezing range of the product was about 36-37° C. The frozen product was a very soft, off-white wax.

Example 18

Soybean Oil+Glycerin+Hexahydrophthalic Anhydride (SYBO-GLY-HHPA 2:1:3)

Soybean oil (1894 g, 2.165 mole) and glycerin (100.0 g, 1.086 mole) were combined in a 3-liter flask equipped as for Example 1 and heated to 180° C. The temperature reached 180° C. about 45 minutes after heating commenced. Dibutyltin dilaurate catalyst (7.00 g, 0.011 mole) was added to the mixture at about 160° C. as it heated up. After about 1 hour at 180° C., there was no visible sign of a separate glycerin phase. Heating at 180° C. was continued for a total of six hours, after which the reaction mixture was allowed to cool under nitrogen and stand at room temperature for three days, during which time the glyceride mixture partially froze. The batch was re-melted by gentle warming and a 400-g portion was removed as a retained sample.

The balance of the batch (1600 g, ~2.606 mole assuming a calculated m.w. of 614 g/mole) was heated to about 55° C. Meanwhile, hexahydrophthalic anhydride (HHPA) was melted in a 40° C. oven. Molten HHPA (364.8 g, 2.366 mole) was added to the diglyceride mixture in a single portion and the resulting mixture heated to 130° C. The batch was sampled intermittently for an acid number analysis. About six hours after the HHPA addition, the acid number had stopped dropping, stalling at a value of 74.5 mg KOH/g, indicating 91.8% reaction of the HHPA. An IR spectrum of the product showed very little remaining anhydride functionality.

The product was a golden-yellow liquid having a Gardner color of 2.8. The viscosity was measured as 127.7 cSt at 40° C. and 15.54 cSt at 100° C. The density was measured as 0.9610 g/cm$^3$ at 49° C. and 0.9821 g/cm$^3$ at 15° C. The pour point of the product was less than −13° C.

Example 19

Coconut Oil+Glycerin (2:1)+Succinic Anhydride (CNTO-GLY-SA 2:1:3)

Molten coconut oil glyceride from Example 7 (168 g, 0.353 mole) and succinic anhydride (32.0 g, 0.320 mole) were weighed directly into a 250-mL flask. The flask was equipped as for Example 1. The mixture was heated to 125° C. over a period of about one hour, during which time the succinic anhydride substantially dissolved. The progress of the reaction was tracked by periodic titration of the acid number and by disappearance of the anhydride absorbance bands in the IR spectrum. After 4.5 hours at 125° C., the acid number had declined to 94.5 mg KOH/g, indicating 94.7% reaction of the succinic anhydride. The anhydride bands in the IR were almost completely gone as well. The reaction mixture was cooled at this point, yielding 99.5% material recovery of slightly hazy yellow oil. There was a small amount of gelatinous residue that settled to the bottom of the flask.

Example 20

Coconut Oil+Glycerin (2:1)+Hexahydrophthalic Anhydride (CNTO-GLY-HHPA 2:1:3)

Molten coconut oil glyceride from Example 7 (155 g, 0.326 mole) and molten HHPA (32.0 g, 0.320 mole) were weighed directly into a 250-mL flask. The flask was equipped as for Example 1. The mixture was heated to 130° C. over a period of about 80 minutes, during which time the reaction mixture turned from turbid to clear. After 5 hours at 130° C., the acid number had declined to 87.6 mg KOH/g, indicating 93% reaction of the anhydride. The anhydride bands in the IR were very small at this point. The total material recovery was 99.6%. The product was a crystal-clear, yellow oil.

Example 21

Coconut Oil+Glycerin (2:1)+methylhexahydrophthalic Anhydride (CNTO-GLY-MHHPA 2:1:3)

Molten product from Example 7 (152 g, 0.320 mole) and MHHPA (48.0 g, 0.285 mole) were added to a 250-mL flask equipped as for Example 1. The mixture was heated to 130° C. over a period of about 80 minutes and held at that temperature for a period of 5.5 hours before cooling. The product had a final acid number of 84.3 mg KOH/g (calculated 95% reaction of MHHPA). The IR spectrum showed very little residual anhydride. The product was a clear, yellow oil at room temperature.

Example 22

Coconut Oil+Glycerin (2:1)+Octenylsuccinic Anhydride (CNTO-GLY-OSA 2:1:3)

Using the same procedure as above, molten Example 7 product (143 g, 0.299 mole) and octenylsuccinic anhydride (57.0 g, 0.269 mole) were heated together at 130° C. for about five hours. The resulting slightly hazy, yellow oil had an acid number of 82.0 mg KOH/g (91% reaction of the OSA). Total recovery of the product was about 99.8%. The IR spectrum was as expected.

Example 23

Rapeseed Oil+Glycerin (1.5:1)+Succinic Anhydride (RPSO-GLY-SA 3:2:5)

Thoroughly mixed product from Example 8 (303 g, 0.527 mole) and succinic anhydride (47.50 g, 0.475 mole) were combined in a 500-mL flask equipped as for Example 1. The 2-phase mixture was warmed from ambient temperature to 120° C. and held at that temperature for a total of 5 hours. The acid number was 78 mg KOH/g, calculated as 97.5% reaction of the succinic anhydride. An IR spectrum of the product confirmed that there was only a trace of unreacted anhydride. The product was a hazy yellow oil with about 2% of a dark gold, dense gelatinous residue that settled to the bottom upon standing. The yield of product was over 99%.

Example 24

Rapeseed Oil+Glycerin (1.5:1)+Hexahydrophthalic Anhydride (RPSO-GLY-HHPA 3:2:5)

The Example 8 product was mixed until visually homogeneous. This material (282 g, 0.490 mole) and molten HHPA (68.0 g, 0.441 mole) were combined in a 500-mL flask set up as for Example 1. The resulting liquid mixture was warmed to 130° C. over a period of about 30 minutes and then held at 130° C. for about 5 hours, at which time the acid number had dropped to 74.4 mg KOH/g, indicating 94.7% reaction of the HHPA. The IR spectrum of the product showed no discernible peaks in the anhydride region. The cooled product was a crystal clear, yellow oil that was recovered in over 99% yield.

Example 25

Rapeseed Oil+Glycerin (1.5:1)+Methylhexahydrophthalic Anhydride (RPSO-GLY-MHHPA 3:2:5)

Well-mixed product from Example 8 (277 g, 0.482 mole) and MHHPA (73.0 g, 0.434 mole) were combined in a 500-mL flask which was equipped as for Example 1. The mixture was heated to 130° C. over a period of about 1 hour during which time the mixture changed from hazy to clear. The reaction was held at 130° C. for a period of 4.5 hours. At the end of this time, the acid number was 73.4 mg KOH/g, indicating 94.5% reaction of the MHHPA. An IR spectrum confirmed that the anhydride had substantially reacted. The product was recovered in nearly quantitative yield as a crystal-clear yellow oil.

Example 26

Rapeseed Oil+Glycerin (1.5:1)+Octenylsuccinic Anhydride (RPSO-GLY-OSA 3:2:5)

Using the same procedure as for Example 25, Example 8 product (263 g, 0.457 mole) was reacted with octenylsuccinic anhydride (87.0 g, 0.410 mole) to yield a clear yellow oil having an acid number of 69.4 mg KOH/g (94.4% reaction) after 4 hours at 130° C. The IR confirmed the absence of any significant unreacted anhydride. The product was a crystal-clear yellow oil that was recovered quantitatively.

C. Organic Salts of Glyceride-Cyclic Carboxylic Acid Anhydride Adducts

Examples 27 through 43 demonstrate how the glyceride-cyclic carboxylic acid anhydride adducts of Examples 9 through 26 can be neutralized with various bases to form exemplary rust-preventive salts.

Example 27

(SYBO-GLY-SA 2:1:3) Salts

Various salts of the soy diglyceride-succinate half-acid ester of Example 9 were prepared by simple mixing of 20-gram portions of the Example 9 product with the bases shown in TABLE 1 in the indicated amounts. The physical appearance of each salt is also noted in the table. Mild heating was applied during the mixing of samples H and J in order to aid the dissolution of these solid bases.

TABLE 1

| Example Salts of SYBO-GLY-SA | | | | |
|---|---|---|---|---|
| Sample | Base | mw | grams | Appearance |
| 27A | 50% aqueous NaOH | 40.00 | 2.20 | Opaque slurry, pale yellow |
| 27B | triethanolamine | 149.19 | 4.11 | Viscous opaque gel, yellow |
| 27C | diethylethanolamine | 117.19 | 3.22 | Clear yellow oil |

TABLE 1-continued

Example Salts of SYBO-GLY-SA

| Sample | Base | mw | grams | Appearance |
|---|---|---|---|---|
| 27D | 2-ethylhexylamine | 129.25 | 3.56 | Clear yellow oil |
| 27E | isododecyloxypropyl-amine | 250.00 | 6.88 | Clear yellow oil |
| 27G | tributylamine | 185.35 | 5.10 | Clear yellow oil |
| 27H | imidazole | 68.05 | 1.87 | Clear yellow oil |
| 27I | 1-methylimidazole | 82.07 | 2.26 | Clear yellow oil |
| 27J | 2-methylimidazole | 82.07 | 2.26 | Clear yellow oil |

These examples illustrate that most organic salts of the Example 9 product are uniform oils, whereas the sodium salt is not.

Example 28

(SYBO-GLY-HHPA 2:1:3) Salts

Various salts of the Example 10 product were prepared by simple unheated mixing of 30-gram portions of that material with the bases shown in TABLE 2 in the indicated amounts. The physical appearance of each salt is noted in the table. The appearance of the calcium salt (28J) is after dilution by 50 wt. with 100-second naphthenic oil. These examples suggest that the inorganic salts and some of the alkanolamine salts (28C, 28D, 28E) have physical forms which may be less desirable for some applications than other organic salts.

TABLE 2

Example Salts of SYBO-GLY-HHPA

| Sample | Base | mw | grams | Appearance |
|---|---|---|---|---|
| Alkali Metal Salts | | | | |
| 28A | 45% aqueous KOH | 56.11 | 4.94 | 2-phase, oil & translucent gel |
| 28B | 50% aqueous NaOH | 40.00 | 3.17 | 2-phase, oil over opaque slurry |
| Amine Salts | | | | |
| 28C | triethanolamine | 149.19 | 5.91 | 2 phase, oil over viscous turbid oil |
| 28D | monoethanolamine | 61.08 | 2.42 | Orange oil w. slight precipitate |
| 28E | 3-amino-1-propanol | 75.11 | 2.97 | Turbid, very viscous oil |
| 28F | 3-methoxypropylamine | 89.14 | 3.53 | Clear yellow oil |
| 28G | diethylethanolamine | 117.19 | 4.64 | Clear orange oil |
| 28H | 2-(2-aminoethoxy)ethanol | 105.14 | 4.16 | Clear golden oil |
| 28I | 2-ethylhexylamine | 129.25 | 5.12 | Clear yellow oil |
| Alkaline Earth Salt | | | | |
| 28J | Calcium oxide | 56.08 | 1.11 | Hard, turbid gel |

Example 29

(SYBO-GLY-MHHPA 2:1:3) Salts

Several salts of Example 11 were produced by mixing 35-gram portions of that material with the bases shown in TABLE 3 in the indicated amounts. The physical appearance of each salt is noted in the table. The appearance of the calcium salt (29J) is after dilution by 50 wt. % with 100-second naphthenic oil.

TABLE 3

Example Salts of SYBO-GLY-MHHPA

| Sample | Base | mw | grams | Appearance |
|---|---|---|---|---|
| Alkali Metal Salts | | | | |
| 29A | 45% aqueous KOH | 56.11 | 5.63 | 2 Yellow oil phases |
| 29B | 50% aqueous NaOH | 40 | 3.61 | White solids in yellow oil |
| Amine Salts | | | | |
| 29C | triethanolamine | 149.19 | 6.74 | Turbid v viscous yellow oil |
| 29D | monoethanolamine | 61.08 | 2.76 | Clear v viscous yellow oil |
| 29E | diethylethanolamine | 117.19 | 5.29 | Clear viscous yellow oil |
| 29F | imidazole | 68.05 | 3.07 | Clear viscous yellow oil |
| 29G | 1-methylimidazole | 82.07 | 3.71 | Clear yellow oil |
| 29H | 2-methylimidazole | 82.07 | 3.71 | Clear yellow oil |
| 29I | 2-ethylhexylamine | 129.25 | 5.84 | Clear yellow oil |
| Alkaline Earth Salt | | | | |
| 29J | Calcium Oxide | 56.08 | 1.27 | Yellow gel with unreacted CaO |

The physical forms exhibited by inorganic salts and some alkanolamine salts (29C) may be undesirable for some applications.

Example 30

(SYBO-GLY-MHHPA 2:1:3) Salts

Example 11 was repeated, yielding a glyceride half-ester/half-acid having an acid number of 71.9 mg KOH/g. This batch was used to produce additional amine salts by mixing 35 g portions of the glyceride half-ester/half-acid with the amines shown in TABLE 4 in the indicated amounts. The physical appearance of each salt is noted in the table.

TABLE 4

Example Salts of SYBO-GLY-MHHPA

| Sample | Base | mw | grams | Appearance |
|---|---|---|---|---|
| 30A | 3-amino-1-propanol | 75.11 | 3.37 | Very viscous yellow oil |
| 30B | 3-methoxypropylamine | 89.14 | 4.00 | Viscous yellow oil |
| 30C | 2-(2-aminoethoxy)ethanol | 105.14 | 4.72 | Viscous yellow oil |
| 30D | 5-amino-1-pentanol | 103.17 | 4.63 | Viscous yellow oil |
| 30E | dimethylethanolamine | 89.14 | 4.00 | Viscous yellow oil |
| 30F | triisopropanolamine, 85% | 191.27 | 10.09 | Turbid, v viscous yellow oil |

Example 31

(SYBO-GLY-MHHPA 2:1:3) Salts

A large-scale preparation combining the steps of Examples 1 and 11 was accomplished by first reacting soybean oil (1518 g, 1.735 mole) and glycerin (80.0 g, 0.869 mole) in the presence of BTEH (1.33 grams, 0.0022 mole) catalyst at 180° C. for five hours. The batch was then cooled to room temperature, and methylhexahydrophthalic anhydride (400.8 g, 2.383 mole) was added. The mixture was then heated to 130° C. for seven hours, during which time the acid number dropped to 70.0 mg KOH/g. An IR spectrum of the product showed a negligible anhydride peak. At total of 1993 g (exclusive of acid number samples) of soy glyceride half ester/half acid was recovered as a clear golden-yellow oil. This material was used to produce additional amine salts similar to Examples 29 and 30 by mixing 35 g portions of the glyceride half-ester/half-acid with the amines shown in TABLE 5 in the indicated amounts.

TABLE 5

Example Salts of SYBO-GLY-MHHPA

| Sample | Base | mw | grams | Appearance |
|---|---|---|---|---|
| 31A | Ammonium hydroxide, 50% | 35.05 | 3.05 | 2-phase, yellow oils |
| 31B | Tetramethyl-ammonium hydroxide, 10% in $H_2O$ | 91.11 | 39.66 | White emulsion over clear yellow aqueous layer |
| 31C | morpholine | 87.12 | 3.79 | Orange gel & yellow oil |
| Tertiary Amines | | | | |
| 31D | triethylamine | 101.19 | 4.40 | White gel & yellow oil |
| 31E | Tributylamine | 185.35 | 8.07 | Yellow gel and reddish oil |
| Secondary Amines | | | | |
| 31F | dibutylamine | 129.25 | 5.63 | Clear orange oil |
| 31G | bis(2-ethylhexyl)amine | 241.46 | 10.51 | Slightly hazy orange oil |
| Primary Amines | | | | |
| 31H | 1-octylamine | 129.25 | 5.63 | Clear yellow oil |
| 31I | 2-ethylhexylamine | 129.25 | 5.63 | Clear golden oil |
| 31J | Primene 81-R | 189.89 | 8.28 | Clear yellow oil |

Examples 29, 30, and 31 show that for this soy-MHHPA glyceride half ester/half acid, the simple inorganic salts (KOH, NaOH, CaO, ammonia) are multi-phase mixtures. Similarly, most of the tertiary amine salts (triethanolamine, triisopropanolamine, triethylamine, tributylamine) gave turbid or semi-gelatinous salts. The secondary amine salts (dibutylamine, bis(2-ethylhexylamine), and morpholine) were higher in color than the primary amine salts.

Example 32

(SYBO-GLY-MHHPA 1:1:2) Salts

Several salts of the Example 12 product were prepared by simple unheated mixing 30 g portions of that material with the bases shown in TABLE 6 in the indicated amounts. The physical appearance of each salt is also noted. The calcium salt (32J) was prepared by diluting the Example 12 calcium oxide mixture to 50 wt. % with 100-second naphthenic oil and heating to ~70° C. with vigorous mixing.

TABLE 6

Example Salts of SYBO-GLY-MHHPA

| Sample | Base | mw | grams | Appearance |
|---|---|---|---|---|
| Alkali Metal Salts | | | | |
| 32A | 45% KOH | 56.11 | 6.14 | Yellow oil |
| 32B | 50% NaOH | 40.00 | 3.94 | Paste with solid precipitate |

TABLE 6-continued

Example Salts of SYBO-GLY-MHHPA

| Sample | Base | mw | grams | Appearance |
|---|---|---|---|---|
| Amine Salts | | | | |
| 32C | Triethanolamine | 149.19 | 7.35 | Very viscous golden oil |
| 32D | Monoethanolamine | 61.08 | 3.01 | Viscous yellow oil |
| 32E | 3-amino-1-propanol | 75.11 | 3.70 | Viscous golden oil |
| 32F | 3-methoxypropylamine | 89.14 | 4.39 | Yellow oil |
| 32G | Diethylethanolamine | 117.19 | 5.77 | Golden oil |
| 32H | 2-(2-aminoethoxy)ethanol | 105.14 | 5.18 | Viscous yellow oil |
| 32I | 2-ethylhexylamine | 129.25 | 6.36 | Yellow oil |
| Alkaline Earth Salts | | | | |
| 32J | Calcium oxide | 56.08 | 1.38 | Turbid, stiff, yellow gel |

It may be noted that the KOH salt is a uniform oil whereas the NaOH salt is not.

Example 33

(SYBO-GLY-ODSA 1:2:3) Salts

Five salts of the Example 13 product were prepared by combining 20 g portions of Example 13 with bases in the amounts shown in TABLE 7.

TABLE 7

Example Salts of SYBO-GLY-ODSA

| Sample | Base | mw | grams | Appearance |
|---|---|---|---|---|
| 33A | diethylethanolamine | 117.19 | 3.33 | Viscous orange liquid |
| 33B | 2-ethylhexylamine | 129.25 | 3.68 | Viscous golden liquid |
| 33C | Imidazole | 68.05 | 1.94 | Very viscous orange liq. |
| 33D | 1-methylimidazole | 82.07 | 2.33 | Viscous golden liquid |
| 33E | Calcium oxide | 56.08 | 0.80 | Viscous turbid gold slurry |

Example 34

(S113-GLY-SA, HHPA, OSA 2:1:3) and (S130-GLY-MHHPA 2:1:3) Salts

Molten 20 g. portions of the products from Examples 14, 15, 16, and 17 were each neutralized with 2 ethylhexylamine (EHAM) by simple unheated mixing in the amounts shown in TABLE 8.

TABLE 8

Example Salts Neutralized with 2-ethylhexylamine

| Sample | Glyceride-Anhydride Adduct | Acid No. mg KOH/g | EHAM grams | Appearance |
|---|---|---|---|---|
| 34A | Example 14 | 70.0 | 3.23 | Soft yellow wax |
| 34B | Example 15 | 71.6 | 3.30 | Soft yellow wax |
| 34C | Example 16 | 68.3 | 3.15 | Soft yellow wax |
| 34D | Example 17 | 69.6 | 3.21 | Soft off-white wax |

This example demonstrates how partial hydrogenation of a vegetable triglyceride can increase the melting point of the derived final product salts. Examples 14-16 originated from Cargill S-113 Wax (Example 4) and Example 17 derives from Cargill S-130 Wax (Example 5). Since S-113 and S-130 are partially hydrogenated soybean oils, Example 27D is an un-hydrogenated analog of Example 34A, Example 28I is an un-hydrogenated analog of Example 34B, and Examples 29I and 31I are replicate un-hydrogenated versions of Example 34D. In all cases, the un-hydrogenated final salts are liquids whereas the Example 34 hydrogenated variants are soft waxy solids.

Example 35

(SYBO-GLY-HHPA 2:1:3) Salts

Several salts of the Example 18 product were prepared by room-temperature mixing of the product with the amines shown in TABLE 9 in the amounts indicated. Each mixture below is calculated to give 0.95 mole of amine per mole of acid in the Example 18 product. The appearance and odor of each salt is also noted.

TABLE 9

Example Amine Salts of Example 18 product

| Sample | Amine | Amine mw | Ex. 18 (g) | Amine (g) | Appearance/ Physical Form | Odor |
|---|---|---|---|---|---|---|
| 35A | 3-amino-1-propanol | 75.11 | 30.0 | 2.84 | Viscous yellow oil | Mild |
| 35B | 2-amino-2-methyl-1-propanol (95%) | 89.14 | 30.0 | 3.55 | Very viscous yellow oil | Mild |
| 35C | 3-methoxypropyl-amine | 89.14 | 30.0 | 3.37 | Yellow oil | Fishy |
| 35D | dimethylethanolamine | 89.14 | 30.0 | 3.37 | Yellow oil | Amine |
| 35E | morpholine | 87.12 | 30.0 | 3.29 | Yellow oil | Amine |
| 35F | methyldiethanol-amine | 119.16 | 30.0 | 4.51 | Viscous yellow oil | None |
| 35G | diethylethanol-amine | 117.19 | 30.0 | 4.43 | Golden oil | Amine |
| 35H | 2-(2-aminoethoxy)-ethanol | 105.14 | 30.0 | 3.98 | Viscous yellow oil | Fishy |
| 35I | 3-dimethylamino-1-propylamine | 100.16 | 30.0 | 3.79 | Yellow oil | Amine |
| 35J | t-butylamine | 73.14 | 30.0 | 2.77 | Yellow oil | Strong Amine |
| 35K | cyclohexylamine | 99.18 | 30.0 | 3.75 | Stiff yellow gel | None |
| 35L | 2-ethylhexylamine | 129.25 | 300.0 | 48.88 | Yellow oil | Mild |
| 35M | monoethanolamine | 61.08 | 30.0 | 2.31 | Viscous yellow oil | Slight Amine |
| 35N | triethanolamine | 149.19 | 30.0 | 5.64 | Very viscous yellow oil | None |

Comparing the physical appearance of the salts in 35A, 35M, and 35N in Example 35 to the corresponding salts of Example 28 (28E, 28D, and 28C) it can be seen that the dibutyltin dilaurate catalyst used to prepare the precursor diglyceride for Example 35 results in products having superior homogeneity.

Example 36

(CNTO-GLY-SA 2:1:3) Salts

Amine salts of the Example 19 product were prepared by simple mixing of 20 g portions of the product with the amines in TABLE 10 in the amounts indicated. The initial appearance of each salt is also noted.

TABLE 10

Example Salts of Example 19 Product

| Sample | Amines | mw | grams | Appearance |
|---|---|---|---|---|
| 36A | triethanolamine | 149.19 | 5.02 | Off-white wax |
| 36B | monoethanolamine | 61.08 | 2.06 | Turbid, yellow oil |
| 36C | 3-methoxypropylamine | 89.14 | 3.00 | Clear, pale yellow oil |
| 36D | diethylethanolamine | 117.19 | 3.95 | Clear, golden oil |
| 36E | 2-(2-aminoethoxy)ethanol | 105.14 | 3.54 | Sl. hazy, pale yellow oil |
| 36F | 3-(dimethylamino)-propylamine | 102.18 | 3.44 | Clear, pale yellow oil |
| 36G | dibutylamine | 129.25 | 4.35 | Clear, pale yellow oil |
| 36H | 1-octylamine | 129.25 | 4.35 | Pale, semi-solid slurry |
| 36I | 2-ethylhexylamine | 129.25 | 4.35 | Clear, pale yellow oil |

All of the salts that were initially clear oils (36C, 36D, 36F, 36G, and 36I) partially froze upon standing at room temperature.

Example 37

(CNTO-GLY-HHPA 2:1:3) Salts

Eleven amine salts of the Example 20 product were prepared by simple mixing of 18 g portions of the product with amines in the amounts shown in TABLE 11. The appearance of each resulting salt was noted immediately after mixing. Several of the salts that were initially clear oils (37D, 37F, 37G, 37H, and 37I) partially froze upon standing; the only exception was the Primene® 81-R salt.

TABLE 11

Example Salts of Example 20 Product

| Sample | Amines | mw | grams | Appearance |
|---|---|---|---|---|
| 37A | triethanolamine | 149.19 | 4.19 | Clear yellow oil over turbid gel |
| 37B | monoethanolamine | 61.08 | 1.72 | Clear yellow oil over turbid gel |
| 37C | 3-methoxypropylamine | 89.14 | 2.50 | Off-white wax |
| 37D | diethylethanolamine | 117.19 | 3.29 | Clear, golden oil |
| 37E | 2-(2-aminoethoxy)ethanol | 105.14 | 2.95 | Clear yellow oil over turbid gel |
| 37F | 3-(dimethylamino)propylamine | 102.18 | 2.87 | Clear, pale yellow oil |
| 37G | dibutylamine | 129.25 | 3.63 | Clear, pale yellow oil |
| 37H | 1-octylamine | 129.25 | 3.63 | Clear, pale yellow oil |
| 37I | 2-ethylhexylamine | 129.25 | 3.63 | Clear, pale yellow oil |
| 37J | Primene® 81-R | 189.89 | 5.35 | Clear, pale yellow oil |

Example 38

(CNTO-GLY-MHHPA 2:1:3) Salts

Eleven amine salts of the Example 21 product were prepared by simple mixing of 18 g portions of the product with amines shown in TABLE 12 in the amounts shown. The appearance of each resulting salt was noted immediately after mixing.

TABLE 12

Example Salts of CNTO-GLY-MHHPA

| Sample | Amines | Mw | grams | Appearance |
|---|---|---|---|---|
| 38A | triethanolamine | 149.19 | 4.19 | Clear yellow oil over turbid gel |
| 38B | monoethanolamine | 61.08 | 1.72 | Clear yellow oil over turbid gel |
| 38C | 3-methoxypropylamine | 89.14 | 2.50 | Off-white wax |
| 38D | diethylethanolamine | 117.19 | 3.29 | Clear, golden oil |
| 38E | 2-(2-aminoethoxy)ethanol | 105.14 | 2.95 | Clear yellow oil over turbid gel |
| 38F | 3-(dimethylamino)propylamine | 102.18 | 2.87 | Clear, pale yellow oil |
| 38G | dibutylamine | 129.25 | 3.63 | Clear, pale yellow oil |
| 38H | 1-octylamine | 129.25 | 3.63 | Clear, pale yellow oil |
| 38I | 2-ethylhexylamine | 129.25 | 3.63 | Clear, pale yellow oil |
| 38J | Primene® 81-R | 189.89 | 5.35 | Clear, pale yellow oil |

Several of the salts that were initially clear oils (38D, 38F, 38G, 38H, and 38I) partially froze upon standing; the only exception was the Primene® 81-R salt.

Example 39

(CNTO-GLY-OSA 2:1:3) Salts

A 2-ethylhexylamine salt of the Example 22 product was prepared by simple mixing of 18 g of the product with 3.4 g of 2-ethylhexylamine. The product was a clear, pale yellow oil that froze into a semi-solid waxy slush when cooled.

Example 40

(RPSO-GLY-SA, HHPA, MHHPA, OSA 3:2:5) Salts

Molten 35 gram portions of the products from Examples 23, 24, 25, and 26 were each neutralized with 2-ethylhexylamine (EHAM) by simple un-heated mixing according to TABLE 13. All salts were initially clear oils.

TABLE 13

Example Salts neutralized with 2-ethylhexylamine

| Sample | Glyceride-Anhydride Adduct | Acid No. mg KOH/g | EHAM grams | Appearance |
|---|---|---|---|---|
| 40A | Example 23 | 78.0 | 6.29 | Clear golden oil |
| 40B | Example 24 | 74.4 | 6.00 | Clear golden oil |
| 40C | Example 25 | 73.4 | 5.92 | Clear golden oil |
| 40D | Example 26 | 69.4 | 5.59 | Clear golden oil |

Example 41

(SYBO-GLY-MHHPA 2:1:3 EHAM) Neutralization Ladder

A duplicate preparation of Example 11 yielded a glyceride half-ester/half acid having an acid number of 72.4 mg KOH/g. Five 15.0-gram portions of this material were combined with different amounts of 2 ethylhexylamine (EHAM) according to TABLE 14 to yield a series having base to acid ratios between 0.8 (80%) and 1.2 (120%). All five materials were clear yellow oils. These examples demonstrate that amine odors from the final neutralized products can be minimized or eliminated by using a slight excess of the free acid to the amine.

TABLE 14

Effect of Varying Amine Concentration

| Sample | EHAM grams | % Neut | Odor |
|---|---|---|---|
| 41A | 2.00 | 80% | Mild |
| 41B | 2.25 | 90% | Mild |
| 41C | 2.50 | 100% | Slight amine |
| 41D | 2.75 | 110% | Pungent amine |
| 41E | 3.00 | 120% | Pungent amine |

Evaluation of Corrosion-Inhibiting Compositions

To be applied to a metal substrate the corrosion inhibitor compound is solubilized in a diluent, such as a volatile organic solvent, petroleum or vegetable oil, or emulsified in water. The corrosion inhibitor properties of these compounds (and existing corrosion inhibitors for comparison) may be assessed using several established methods, as described below:

1. Accelerated Weathering

Accelerated weathering tests were performed according to ASTM D4585-07 Standard Practice for Testing Water Resistance of Coatings Using Controlled Condensation, using a QCT condensation tester, obtained from Q-Lab Corporation, Westlake, Ohio. The QCT cabinet applies continuous, controlled-temperature, warm-water condensation to the test surface. In the test, thin metal panels with a standard surface finish are held at an angle of 30° from vertical over a pool of heated water, in an atmosphere at 46° C. As the metal panels, steel test panels "Q-Panels," were obtained from Q-Lab Corporation. Two types of panels were employed, both made from standard low-carbon, cold-rolled steel compliant with ASTM A1008/1010. Type QD-36 panels have a smooth, polished, bright finish representative of finely finished metal, whereas type R-36 panels have a rougher, dull-matte finish that is representative of general sheet-metal applications. These panels, measuring approx. 7.6×15.2 cm, were coated by dipping them into various solutions or emulsions of the corrosion-inhibiting compositions to be tested. The coated panels were allowed to drip-dry at room temperature overnight (or longer). The corrosion-inhibiting properties of the applied coatings were then assessed by placing the panels on the test stand of the QCT cabinet and periodically inspecting the panels for the presence of visible rust. Rust spots that touch an edge of the panel and extend less than ⅛" (~3 mm) inward from the edge are ignored because the panel edges tend to be scraped during the examination process and this can lead to removal of the corrosion inhibitor coating and premature rusting along the edges.

2. Water Displacement and Water Separation

Desirable ancillary properties for a corrosion inhibitor compound that is to be applied using an organic solvent are the ability of the solution to displace water and the ability to separate water. Many metalworking fluids, especially so-called synthetic and semi-synthetic types and soluble oils, contain significant amounts of water. An organic solvent solution of a corrosion inhibitor compound should be able to displace the aqueous metalworking fluid residues from the metal part which is to be protected. Otherwise, any aqueous residue that remains on the part may eventually lead to localized corrosion. Furthermore, it is desirable that the aqueous phase thus displaced is not emulsified into the corrosion inhibitor solution, i.e., the displaced aqueous phase should cleanly separate from the organic corrosion inhibitor solution.

Water separation ability is assessed by combining a solution of the test substance in an organic solvent with a measured amount of water, mixing the two phases together, and then timing how long it takes for the water to fully separate from the organic phase. The appearance of the water and solvent layers is also noted at the end of the test, clear aqueous and organic phases suggesting less intermixing than hazy or turbid phases. Generally, 75 mL of organic solvent solution and 25 mL of tap water are tested in this manner in a 100-mL graduated cylinder at room temperature. The cylinder is inverted six times to mix the water and solvent initially. The concentration of the test substance in the organic solvent is also determined.

Performance Results

In the following examples, steel test panels were placed on the QCT test stand and exposed to a water-saturated atmosphere at 46° C. until rust spots were noted in the critical area (exposed surface of the panel, 0.3 cm from the edges). The time to failure (in days) was noted. The steel test panels were of two types: Type QD-36 panels with a smooth, polished surface, and Type R-36 with a rough, matte surface. The panel type used in each example is noted.

Aqueous Emulsion-Applied Corrosion Inhibitors

Example A

Aqueous Emulsion-Applied Corrosion Inhibiting Compositions on Polished Steel

TABLE 15 shows the performance results for several of the example corrosion inhibiting compounds applied with water as the carrier solvent on polished QD-36 steel panels. The test panels were dipped into freshly-agitated aqueous emulsions of the indicated test substances and dried at ambient temperature. The table also shows comparable results for Aqualox® 2268S rust preventive compound, available from Lubrizol Corp. Aqualox® 2268S is designed to be applied as an aqueous emulsion in this manner.

TABLE 15

Performance Results for Aqueous Emulsion-Applied Rust Preventives on Polished Steel

| Test Substance | Glyceride | Anhydride Cap | Neutralizing Base | wt. % in Emul | Coated Panel Appearance | Time to Failure (days) | |
|---|---|---|---|---|---|---|---|
| 29A | SYBO-GLY 2:1 | MHHPA | KOH | 10.0%[a] | Edge dewetting | 9 | |
| | | | | 15.0%[a] | Edge dewetting | 28[b] | |
| | | | | 20.0%[a] | Edge dewetting | 0.2 | 0.04 |
| 29B | SYBO-GLY 2:1 | MHHPA | NaOH | 6.0%[a] | Edge dewetting | 0.3 | |
| | | | | 8.0%[a] | Edge dewetting | 1.0 | |
| | | | | 10.0%[a] | Edge dewetting | 49 | 31 |
| 29C | SYBO-GLY 2:1 | MHHPA | triethanolamine | 10.0% | Edge dewetting | 0.1 | |
| | | | | 10.0% | Mottled | 0.2 | 0.2 |
| | | | | 15.0% | Mottled | 1.1 | 1.1 |
| | | | | 20.0% | Uniform film | 5.0[c] | 5.1[c] |
| 29D | SYBO-GLY 2:1 | MHHPA | monoethanolamine | 10.0%[a] | Edge dewetting | 0.1 | |
| | | | | 20.0%[a] | Moderate dewetting | 0.1 | 0.04 |
| 29E | SYBO-GLY 2:1 | MHHPA | diethylethanolamine | 10.0%[a] | Uniform glossy | [c] | [c] |
| | | | | 15.0%[a] | Uniform glossy | [c] | [c] |
| | | | | 20.0%[a] | Uniform film | 5.1[d] | 5.1[d] |
| 30A | SYBO-GLY 2:1 | MHHPA | $NH_2(CH_2)_3OH$ | 10.0%[a] | Edge dewetting | >5 | >5 |
| 30B | SYBO-GLY 2:1 | MHHPA | $NH_2(CH_2)_3Ome$ | 10.0%[a] | Edge dewetting | >5 | >5 |

TABLE 15-continued

Performance Results for Aqueous Emulsion-Applied Rust Preventives on Polished Steel

| Test Substance | Glyceride | Anhydride Cap | Neutralizing Base | wt. % in Emul | Coated Panel Appearance | Time to Failure (days) | |
|---|---|---|---|---|---|---|---|
| 30C | SYBO-GLY 2:1 | MHHPA | AEE | 10.0%[a] | Edge dewetting | >5 | >5 |
| 30D | SYBO-GLY 2:1 | MHHPA | NH$_2$(CH$_2$)$_5$OH | 10.0%[a] | Severe dewetting | >5 | 1.0 |
| 30E | SYBO-GLY 2:1 | MHHPA | DMEA | 10.0%[a] | Edge dewetting | >5 | >5 |
| 30F | SYBO-GLY 2:1 | MHHPA | TIPA | 10.0%[a] | Severe dewetting | 0.1 | 0.1 |
| | Aqualox® 2268S | | | 10.0% | Moderate dewetting | 0.04 | 0.1 |
| | | | | 10.0% | Moderate dewetting | 0.1 | 0.1 |
| | | | | 10.0% | Moderate dewetting | 0.1 | 0.1 |

Notes for TABLE 15:
[a]Some separation or creaming of emulsion over time
[b]Edges (non-critical area) failed rapidly and completely due to edge dewetting.
[c]Left gray, non-rust stain spots on panel. Appeared early in test.
[d]Failure called on brown spots that appeared to be rust but were actually oily spots. Left gray non-rust stains under these spots.

Examples 30A-F at 10% in water were tested side-by-side with Aqualox® 2268S at 10% for five days. At the end of the five-day test, the exposed panel surfaces were cleaned with isopropyl alcohol and compared side-by-side. Visual rank-ordering of the panels from best to worst was as follows: 30C>30A, 30B>Aqualox® 2268S>30E>30D>>30F Observations on the individual panels in this side-by-side comparison were as follows:

30A: Light discoloration band in center of panel

30B: Light discoloration band in center of panel

30C: Very faint discoloration

30D: Mottled appearance

30E: Obvious stains in a streaked pattern, center of panel

30F: Severe stain spots, center discoloration, and edge rust

Aqualox® 2268S: Edge rust (~0.6 cm) and patchy top rust

Example B

Aqueous Emulsion-Applied Corrosion Inhibiting Compositions on Rough Steel

TABLE 16 shows the performance results for several of the example corrosion inhibitor compounds on rough-finish R-36 steel panels. The test substances were again applied as aqueous emulsions, then dried. Aqualox® 2268S was again used as a comparative example of a conventional emulsion-type corrosion inhibitor.

TABLE 16

Comparative Results for Aqueous Emulsion-Applied Corrosion Inhibiting Compositions on Rough Finish Steel

| Test Substance | Glyceride | Anhydride Cap | Neutralizing Base | wt. % in Emulsion | Time to Failure (days) |
|---|---|---|---|---|---|
| 36C | CNTO-GLY 2:1 | SA | NH$_2$(CH$_2$)$_3$Ome | 5.0%[a] | 9.3 |
| | | | | 10.0%[a] | 10 |
| | | | | 20.0%[a] | >28 |
| 36D | CNTO-GLY 2:1 | SA | diethyl-ethanolamine | 5.0%[a] | 10 |
| | | | | 10.0%[a] | 9.3 |
| | | | | 20.0%[a] | >28 |
| 36F | CNTO-GLY 2:1 | SA | DMAPA | 5.0%[a] | 9.0 |
| | | | | 10.0%[a] | 9.3 |
| | | | | 20.0%[a] | 17 |
| 37F | CNTO-GLY 2:1 | HHPA | DMAPA | 5.00%[a] | 8.0 |
| | | | | 10.0%[a] | >27 |
| | | | | 20.0%[a] | >27 |
| | Aqualox® 2268S | | | 10.0% | 9.0, 9.3 |

All the coated panels had a uniform matte appearance.

In TABLE 16 above, Examples 36C, 36D, 36F, and 37F at 5%, 10%, and 15% in water were tested side-by-side against 10% Aqualox® 2268S on R-36 panels for 28 days. At the end of the test, the exposed panel surfaces were compared side-by-side. In all cases, the results suggest that the Example compounds protected the test panels better than the reference Aqualox® 2268S at equal or lower concentration (bearing in mind that such accelerated tests do not always accurately predict results for actual exposures). Prior to running these tests, the average film thickness of the dried rust preventive films was estimated for Example compounds 36C, 36D, and 36F and Aqualox® 2268S by weighing the panels before and after coating and knowing the approximate density of the dry corrosion inhibiting compounds. These estimated film thicknesses as a function of wt. % of the test substance in the applied emulsion are shown in the FIGURE. This suggests that the superior rust preventive performance of Examples 36C, 36D, and 36F relative to Aqualox® 2268S is accomplished at equal or lower film thickness.

Example C

Example 27 Compounds in an Emulsion Base-Type Corrosion Inhibiting Composition TABLE 17 shows the results of using two of the compounds illustrated in Example 27 as corrosion inhibitors applied as part of an emulsion base package with water as the carrier solvent. The emulsion base package consisted of 25 wt. % of the test substance, 5 wt. % diethylene glycol monobutyl ether, and 70 wt. % 200 SUS naphthenic oil. The emulsion base package was then diluted with water to form an emulsion that was used to coat type QD-36 test panels which were air-dried prior to testing. The last two lines of Example C show comparison results for Aqualox® 2290 AS, a corrosion inhibitor compound available from Lubrizol Corp. Aqualox 2290 AS is designed to be applied as part of an emulsion base package in this manner.

TABLE 17

Comparative Results for Emulsion Base-type Corrosion Inhibiting Compositions

| Test Substance | Glyceride | Anhydride Cap | Neutralizing Base | Emul. Base Wt. % | Solution Appearance | Coated Panel Appearance | Days to Failure | |
|---|---|---|---|---|---|---|---|---|
| 27B | SYBO-GLY 2:1 | SA | triethanolamine | 10.0% | Emulsion$^a$ | Oily w. streaks | 23 | 23 |
| | | | | 20.0% | Emulsion$^a$ | Oily w. waves | 28 | 28 |
| 27C | SYBO-GLY 2:1 | SA | diethylethanolamine | 10.0% | Emulsion$^a$ | Oily, mottled | 21 | 21 |
| | | | | 20.0% | Emulsion$^a$ | Oily, slightly mottled | 21 | 21 |
| | Aqualox ® 2290AS | | | 10.0% | Tan emulsion | Oily w. dry edges | 2 | 2 |
| | | | | 20.0% | Tan emulsion | Uniform oily | 21 | 21 |

Note:
$^a$Slight separation or creaming of emulsion over time.

Solvent and Oil-Applied Corrosion Inhibitors

In the following examples, the corrosion inhibitor compounds are dissolved in volatile organic solvents or non-volatile oils for application to the test panels. As with the aqueous emulsion-applied corrosion inhibitors described previously, the coated test panels are allowed to air dry prior to testing on the QCT stand.

Example D

Ca-Salt of Glyceride Half-Acid Ester Vs. Amine Salt of Glyceride Half-Acid Ester TABLE 18 compares three corrosion inhibiting compositions applied to polished QD-36 steel test panels using mineral spirits as the carrier solvent. A Ca-salt glyceride half-acid ester and an amine salt glyceride half-acid ester were used as the exemplary compounds. Alox® 165, a calcium sulfonate-based corrosion inhibitor compound commercially available from Lubrizol Corporation was used for comparison. Alox® 165 is designed to be applied using volatile organic solvents in this manner, and 5 wt. % of this material in solution is a typical recommended usage level.

TABLE 18

Comparative Results for Solvent-Based Corrosion Compositions

| Test Substance | Glyceride | Anhydride Cap | Neutralizing Base | wt. % in Soln | Solution Appearance | Days to Failure | |
|---|---|---|---|---|---|---|---|
| 29I | SYBO-GLY 2:1 | MHHPA | EHAM | 2.5% | Clear, colorless | 4.9 | 5.0 |
| 29J | SYBO-GLY 2:1 | MHHPA | CaO | 2.5% | Hazy, slight precip. | 2.2 | 2.2 |
| | Alox ® 165 | | | 5.0% | Clear, brown | 1.0 | 1.9 |

All the coated panels had a uniform, glossy appearance.
Example D indicates that the organic amine salt (29I) gives over twice the protection time as the corresponding calcium salt (29J). However, the calcium salt was not completely soluble in mineral spirits. Calcium salts have traditionally been used in many existing corrosion inhibitor compounds. Example 29I product gives significantly longer protection than the Alox® 165 corrosion inhibitor, under the test conditions, when used at one-half the application level.

Example E

Inorganic Salt Vs. Hydrophilic Amine Salt Vs. Hydrophobic Amine Salt

The QD-36 type test panels and mineral spirits as the carrier solvent were again used for testing the corrosion inhibitor compounds. All the coated panels had a uniform, glossy appearance.

The results in TABLE 19 suggest that for an organic solvent-applied corrosion inhibitor application, hydrophobic amines such as 2-ethylhexylamine (EHAM) are better than hydrophilic amines, as exemplified in this case by 3 methoxypropylamine, for the choice of the neutralizing base (all samples of the Example 29 products use SYBO-GLY 2:1 as the glyceride and MHHPA as the anhydride cap). This example also suggests that both the hydrophilic and hydrophobic amine types are superior to inorganic bases, here exemplified by sodium hydroxide. Regardless of the neutralizing base chosen, the glyceride-cyclic carboxylic acid anhydride adducts outperform the existing material, Alox® 165, under the test conditions.

TABLE 19

Comparative Results for Inorganic salt, Hydrophilic Amine Salt and Hydrophobic Amine Salt

| Test Substance | Neutralizing Base | wt. % in Soln | Solution Appearance | Days to Failure | |
|---|---|---|---|---|---|
| 29B | NaOH | 2.5% | Hazy bottom layer | 4.0 | 6.0 |
| 30B | $NH_2(CH_2)_3Ome$ | 2.5% | Clear, colorless | 6.0 | 6.0 |
| 29I | 2-ethyl hexyl-amine (EHAM) | 1.75% | Clear, colorless | >42 | >42 |
|  |  | 1.50% | Clear, colorless | 16 | >42 |
|  |  | 1.25% | Clear, colorless | 24 | >42 |
|  |  | 1.00% | Clear, colorless | 7.9 | 24 |
|  | Alox ® 165 | 5.0% | Clear, gold | 1.9 | 4.0 |

Example F

Concentration Ladder to Establish Concentration Threshold

Smooth QD-36 panels were used as the substrate and the test substance was applied at different concentrations using Isopar M as the carrier solvent. Isopar M is a 92° C. flash point isoparaffinic solvent commercially available from Exxon Mobil Chemical Company. Results are shown in TABLE 20.

TABLE 20

Comparative Results for Different Concentrations of Compound

| Test Substance | Glyceride | Anhydride Cap | Neutralizing Base | wt. % in Soln | Solution Appearance | Days to Failure |
|---|---|---|---|---|---|---|
| 30E | SYBO-GLY 2:1 | MHHPA | dimethyl-ethano-lamine | 4.0% | Hazy | 14 |
|  |  |  |  | 3.0% | Turbid | 14 |
|  |  |  |  | 2.0% | Turbid | 1.0 |
|  |  |  |  | 1.0% | Turbid | 0.17 |
|  |  |  |  | 0.5% | Hazy | 0.13 |
|  |  |  |  | 0.25% | Hazy | 0.07 |

All coated panels had a uniform, glossy appearance.

TABLE 20 illustrates that the rust preventive performance of this particular substance (Example 30E) increases dramatically at an application level of about 2 wt. %. Above this threshold the performance is not seen to increase significantly. It will be expected that for each particular corrosion inhibitor compound described herein it is desirable to apply the material at a level at or above its concentration threshold in order to achieve optimal rust protection, which may differ from that for the 30E corrosion inhibitor compound.

Example G

Effect on Protection Time Above Threshold

Polished QD-36 panels and Isopar M as the application solvent were used. Samples of the products of Example 27 (using SYBO-GLY 2:1 as the glyceride and SA as the anhydride cap) were combined with the solvents in different concentrations. All of the tests shown in TABLE 21 are above the concentration threshold for the respective test substance. For some samples, duplicate test panels were tested. The results suggest that increasing the application level above the concentration threshold does not yield a significant improvement in the protection time on polished surfaces such as the QD-36 panels under the test conditions used.

TABLE 21

Comparative Results of Tests Above the Concentration Threshold

| Test Substance | Neutralizing Base | wt. % in Soln | Solution Appearance | Days to Failure | |
|---|---|---|---|---|---|
| 27C | diethyl-ethanolamine | 5.0% | Clear, yellow | 21 | |
|  |  | 2.5% | Clear, yellow | 24 | |
| 27D | 2-ethyl-hexylamine | 5.0% | Clear, colorless | 21 | |
|  |  | 2.5% | Slightly hazy | 21 | |
| 27E | PA-16 | 5.0% | Clear, colorless | 23 | |
|  |  | 2.5% | Clear, colorless | 23 | |
| 27H | imidazole | 5.0% | Clear[a] | 24 | 21 |
|  |  | 4.0% | Clear[a] | 18 | 25 |
|  |  | 3.5% | Clear[a] | 21 | 21 |
|  |  | 3.0% | Clear[a] | 18 | 21 |
|  |  | 2.5% | Clear[a] | 21 | 21 |
|  |  | 2.0% | Clear[a] | 18 | 18 |
| 27I | 1-methyl imidazole | 4.0% | Hazy | 23 | 23 |
|  |  | 3.0% | Hazy | 21 | 22 |
|  |  | 2.0% | Hazy | 24 | 24 |
| 27J | 2-methyl imidazole | 4.0% | Clear, colorless | 17 | 23 |
|  |  | 3.0% | Clear, colorless | 14 | 21 |
|  |  | 2.0% | Clear, colorless | 14 | 17 |

Note:
[a]Some haze forming in the solution over time.

Example H

Concentration Effect for Soy Vs. Hydrogenated Soy on Rough Panels

In this example, rough R-36 panels were used as the test substrate. The corrosion inhibitors were applied as solutions in mineral spirits and dried overnight. Results are shown in TABLE 22. The results suggest that the corrosion inhibitor derived from soybean oil glyceride gives significantly longer time to failure than the corresponding hydrogenated soybean oil glyceride. This example also suggests that about 1 wt. % of the Example 29I product performs almost as well as 5 wt. % of the Alox® 165 corrosion inhibitor on the type R-36 panels under these conditions. Furthermore it may be noted that comparing the results for the Example 29I product in this example with analogous results on polished QD-36 panels, a higher application level is required to achieve the same protection time on the rough R-36 panels. Also, leveling off of the protection time above a threshold concentration (as was seen on polished panels) is not observed on the rough R-36 panels.

TABLE 22

Concentration Effect for Soy vs. Hydrogenated Soy on Rough Panels

| Test Substance | Glyceride | Anhydride Cap | Neutralizing Base | wt. % in Soln | Solution Appearance | Days to Failure |
|---|---|---|---|---|---|---|
| 29I | SYBO-GLY 2:1 | MHHPA | 2-ethylhexylamine (EHAM) | 1.0% | Clear, colorless | 4.2 |
|  |  |  |  | 2.0% | Clear, colorless | 19 |
|  |  |  |  | 4.0% | Clear, colorless | 38 |
|  |  |  |  | 6.0% | Clear, colorless | >46 |
| 34D | S130-GLY 2:1 | MHHPA | 2-ethylhexylamine (EHAM) | 1.0% | Clear, colorless | 0.08 |
|  |  |  |  | 2.0% | Clear, colorless | 0.13 |
|  |  |  |  | 4.0% | Clear, colorless | 6.0 |
|  |  |  |  | 6.0% | Clear, colorless | 10 |
|  |  | Alox ® 165 |  | 5.0% | Clear, brown | 5.0 |

Example I

Three Glyceride-Anhydride Adducts Neutralized with Four Bases

In this example, polished QD-36 test panels were coated with 1 wt. solutions of various example corrosion inhibitors in mineral spirits. Results are shown in TABLE 23. Failure times that are noted as being less than four days are greater than 1.3 days (failures occurred over a weekend).

TABLE 23

Comparative results for Three Glyceride-Anhydride Adducts Neutralized with Four Bases

| Test Substance | Glyceride | Anhydride Cap | Neutralizing Base | Solution Appearance | Coated Panel Appearance | Days to Failure | |
|---|---|---|---|---|---|---|---|
| 28A | SYBO-GLY 2:1 | HPPA | KOH | Clear, colorless | Uniform glossy | 0.13 | 0.13 |
| 28F |  |  | $NH_2(CH_2)_3Ome$ | Clear, colorless | Uniform glossy | 1.3 | <4 |
| 28I |  |  | EHAM | Clear, colorless | Uniform glossy | <4 | 4.0 |
| 28J |  |  | CaO | Hazy, slight precipitate | Matte w. particles | <4 | 4.0 |
| 29A | SYBO-GLY 2:1 | MHHPA | KOH | Clear, colorless | Uniform glossy | 0.33 | 0.29 |
| 30B |  |  | $NH_2(CH_2)_3Ome$ | Clear, colorless | Uniform glossy | 1.3 | <4 |
| 29I |  |  | EHAM | Clear, colorless | Uniform glossy | <4 | <4 |
| 29J |  |  | CaO | Hazy, slight precipitate | Matte w. particles | 1.3 | <4 |
| 32A | SYBO-GLY 1:1 | MHHPA | KOH | Clear, colorless | Uniform glossy | 0.13 | 0.21 |
| 32F |  |  | $NH_2(CH_2)_3Ome$ | Clear, colorless | Uniform glossy | <4 | <4 |
| 32I |  |  | EHAM | Clear, colorless | Uniform glossy | <4 | <4 |
| 32J |  |  | CaO | Clear, colorless | Uniform glossy | 1.0 | 1.3 |

In the Example I series, three different glyceride-anhydride adducts were each neutralized with four different bases: potassium hydroxide, 3-methoxypropylamine (a hydrophilic amine), 2-ethylhexylamine or EHAM (a hydrophobic amine), and calcium oxide. For all three glyceride-anhydride combinations, the KOH salt gave the least rust protection. The other three salts were more comparable in their protection times, however, the Ca salts were not entirely soluble in mineral spirits for the first two glyceride-anhydride combinations. The third combination, having a lower ratio of soybean oil to glycerin in the glyceride, gave a soluble Ca salt, but this salt failed to give as much rust protection as the amine salts. The results suggest, therefore, that organic amine salts give a superior combination of solvent solubility and rust protection when compared to the equivalent inorganic salts.

Example J

Three Glycerides with Four Different Anhydride Caps, 2-Ethylhexylamine Salts R-36 panels were used as the test substrate. The test substances were all applied to the panels as 0.75 wt. % solutions in mineral spirits and dried for three days prior to testing. In all cases, the neutralizing base is 2-ethylhexylamine. TABLE 25 shows the results obtained.

This example suggests that the best-performing anhydride cap varies depending on the glyceride with which it is reacted. This example further suggests that the coconut oil-derived corrosion inhibitors do not protect as well (taken as a group) as do the soy and rapeseed oil-derived products.

Water separation tests were also conducted on the Example J materials. In the water separation test, 75 mL of a 0.75 wt. % solution of the test substance is combined with 25 mL of water in a graduated cylinder. The cylinder is inverted six times, and then allowed to stand. The time for greater than 24 mL of water to separate as a bottom phase is noted in TABLE 25, along with the appearance of the water and solvent layers after separation. Desirable performance in this test is fast water separation yielding clear aqueous and solvent phases. The data suggests that the succinic anhydride-capped materials taken as a group have inferior water separation. The OSA-capped materials leave a foam "cuff" at the interface between the aqueous and solvent phases in the water separation test.

TABLE 25

Comparative Results for Three Glycerides with Four Caps, 2-ethylhexylamine Salts

| Test Substance | Glyceride | Anhydride Cap | Days to Failure | Water Separation Time (sec) | Notes |
|---|---|---|---|---|---|
| 36I | CNTO-GLY 2:1 | SA | 2.3 | 450 | Slightly hazy water and turbid solvent |
| 37I | | HHPA | 1.1 | 220 | Clear water, hazy solvent |
| 38I | | MHHPA | 1.0 | 220 | Clear water with loose emulsion layer and turbid solvent |
| 39 | | OSA | 2.3 | 200 | Clear water, clear solvent with foam "cuff" at interface |
| 22D | SYBO-GLY 2:1 | SA | 3.1 | >1200 | Hazy water and solvent emulsion |
| 28I | | HHPA | 3.0 | 150 | Clear water, hazy solvent |
| 31I | | MHHPA | 3.0 | 120 | Clear water and clear solvent |
| 40A | RPSO-GLY 3:2 | SA | 2.3 | >1200 | Hazy water and solvent emulsion |
| 40B | | HHPA | 3.1 | 120 | Clear water and clear solvent |
| 40C | | MHHPA | 3.1 | 110 | Clear water and clear solvent |
| 40D | | OSA | 2.3 | 300 | Clear water, clear solvent with foam "cuff" at interface |

Example K

Effect of Solvent on Performance

The Example 29I product SYBO-GLY 2:1 as the glyceride, MHHPA as the anhydride cap, and 2-ethylhexyl amine (EHAM) as the neutralizing base) was applied as a corrosion inhibitor to type QD-36 polished panels using different organic solvents and different concentrations. The results are shown in TABLE 26, with the Alox® 165 corrosion inhibitor used for comparison. The results suggest that the Example 29I product significantly outperforms the existing corrosion inhibitor Alox® 165 on smooth QD-36 panels at equal or lower use levels in mineral spirits. This example further suggests that the performance of the Example 29I product is deleteriously affected when non-volatile oils are used to apply the corrosion inhibitor to the test panel. A large jump in the protection time was observed for the Example 29I product applied with mineral spirits from 0.75% to 2%. This is another example of the concentration threshold effect on the polished QD-36 panels.

TABLE 26

Comparative results for Effect of Solvent on Performance

| Test Substance | Diluent | wt. % in Soln | Days to Failure | |
|---|---|---|---|---|
| 29I | Mineral Spirits | 5.0% | 52 | >65 |
| | | 4.0% | 52 | >65 |
| | | 3.0% | 23 | >65 |
| | | 2.0% | 11 | 21 |
| | | 0.75% | 1.0 | 1.0 |

TABLE 26-continued

Comparative results for Effect of Solvent on Performance

| Test Substance | Diluent | wt. % in Soln | Days to Failure | |
|---|---|---|---|---|
| | | 0.50% | 0.13 | 0.15 |
| | | 0.25% | 0.08 | 0.08 |
| | | 0.13% | 0.05 | 0.05 |
| | Isopar M | 2.5% | 21 | 0.23 |
| | Paraffinic Oil, 100 SUS | 2.5% | 0.23 | 0.13 |
| | Soybean Oil | 2.5% | 0.03 | 0.03 |
| Alox ® 165 | Mineral Spirits | 5.0% | 1.1 | 2.0 |
| | | 5.0% | 1.3 | 2.0 |

Example L

Corrosion Inhibitors Using ODSA as the Anhydride

In this example, QD-36 panels were used and Isopar M as the application solvent for the test substances. Results are shown in TABLE 27. This example suggests that octadecenyl succinic anhydride (ODSA) as the anhydride reactant results in products that do not perform better than the Alox® 165 corrosion inhibitor (although a lower concentration was used). Without being bound by any particular theory, it is hypothesized that, compared with other anhydrides, the bulky octadecenyl moiety in close proximity to the carboxylate functionality may interfere with the ability of the carboxylate to bind effectively with the surface of the steel substrate, therefore resulting in a less-protective film.

C>B~D>A~E. There was very little difference in the rust coverage on panels 41B, 41C, and 41D. This example suggests that 10% under- or over-neutralization of the glyceride-cyclic carboxylic acid anhydride adducts by an organic amine does not markedly affect the rust preventive perfor-

TABLE 27

Comparative results for Corrosion Inhibitors Using ODSA as the Anhydride

| Test Substance | Glyceride | Anhydride Cap | Neutralizing Base | wt. % in Soln | Solution Appearance | Coated Panel Appearance | Days to Failure | |
|---|---|---|---|---|---|---|---|---|
| 33A | SYBO-GLY 1:2 | ODSA | diethyl-ethanolamine | 2.5% | Clear, yellow | Note[a] | <4 | <4 |
| 33B | | | EHAM | 2.5% | Clear, yellow | Note[a] | 1.0 | <4 |
| 33C | | | imidazole | 2.5% | Clear, yellow | Note[a] | <4 | <4 |
| 33D | | | 1-methylimidazole | 2.5% | Clear, yellow | Note[a] | <4 | <4 |
| 33E | | | CaO | 2.5% | Turbid | Note[a] | <4 | <4 |
| | | | Alox ® 165 | 5.0% | Clear, brown | Uniform glossy | <4 | <4 |

Note:
[a]Glossy with ~1.3 cm darker band at bottom of panel

Example M

Corrosion Inhibitors Using Hydrogenated Soybean Glyceride

In this example, mineral spirits was used as the carrier solvent for application of the corrosion inhibitors to QD-36 panels. Results are shown in TABLE 28. This example suggests that good corrosion inhibitors can be produced from partially hydrogenated soybean oil (in this instance Cargill S-113 Wax), however, the partially hydrogenated soybean oil appears to confer no significant performance advantage over soybean oil itself.

TABLE 28

Comparative results for Corrosion inhibitors Using Hydrogenated Soybean Glyceride

| Test Substance | Glyceride | Anhydride Cap | Neutralizing Base | wt. % in Soln | Solution Appearance | Days to Failure | |
|---|---|---|---|---|---|---|---|
| 29I | SYBO-GLY 2:1 | MHHPA | 2-ethylhexylamine (EHAM) | 1.0% | Clear, colorless | 2.0 | 2.0 |
| 34B | S113-GLY 2:1 | HHPA | | 1.0% | Clear, colorless | 1.0 | 1.0 |
| 34C | S113-GLY 2:1 | OSA | | 1.0% | Clear, colorless | 1.0 | 1.3 |
| 34A | S113-GLY 2:1 | SA | | 1.0% | Clear, colorless | >2.0 | 2.0 |
| | | | Alox ® 165 | 5.0% | Clear, brown | 1.0 | 1.3 |

Example N

Effect of Neutralization

Examples 41A-E were each dissolved at 1 wt. % in mineral spirits and these solutions were used to coat QD-36 panels which were tested on the QCT for three days after drying. At the end of the three-day test, the panels were visually compared. All five panels were past failure at that point, with partial rust coverage on all of the panels. Rank ordering of these panels from best to worst was mance. Slight under-neutralization (i.e., an excess of acid) is therefore practical because odors due to free amine are minimized.

Example O

Effect of Solvent Volatility

For this example, Example compound 29I (SYBO-GLY 2:1 as the glyceride, MHHPA as the anhydride cap and 2-ethylhexyl amine (EHAM) as the neutralizing agent) was dissolved at 10 wt. % in a series of hydrocarbon solvents of varying volatility as well as in a non-volatile paraffinic oil.

These solutions were used to coat rough R-36 panels. The Exxsol™ solvents shown in TABLE 29 are commercially available dearomatized aliphatic solvents available from ExxonMobil Chemical Company. The boiling ranges and evaporation rates of these solvents (relative to butyl acetate) were taken from ExxonMobil literature. Results shown in TABLE 29 suggest that the protection time increases as the volatility of the solvent increases. The protection time using the non-volatile paraffinic oil was relatively low. These results suggest that residual solvent or oil may have a deleterious impact on the corrosion inhibiting films.

TABLE 29

Effect of Solvent Volatility

| Test Substance | Solvent | Solv. lower b.p. (° C.) | Solv. upper b.p. (° C.) | Evap Rate (BuAc = 100) | Days to Fail |
|---|---|---|---|---|---|
| 29I | Exxsol D40 | 161 | 198 | 18 | 68 |
|  | Exxsol D60 | 190 | 211 | 6 | 46 |
|  | Exxsol D80 | 208 | 234 | 1.8 | 18 |
|  | Exxsol D95 | 225 | 239 | 0.7 | 19 |
|  | Paraffinic Oil, 100 Neutral |  |  |  | <3 |

Example P

Effect of Hydrophobic Amine Choice

In this example, mineral spirits was used as the carrier solvent for applying the test substances to R-36 panels. Results are shown in TABLE 30. This example shows that the protection time is influenced by the choice of the neutralizing amine, even when structurally similar hydrophobic amines are compared.

TABLE 30

Effect of Hydrophobic Amine Choice

| Test Substance | Glyceride | Anhydride Cap | Neutralizing Base | wt. % in Soln | Days to Failure |
|---|---|---|---|---|---|
| 31E | SYBO-GLY | MHHPA | Bu$_3$N | 1.0% | 41 |
| 31F | 2:1 |  | Bu$_2$NH | 1.0% | >60 |
| 31H |  |  | octylamine | 1.0% | >60 |
| 31I |  |  | EHAM | 1.0% | 26 |
| 31J |  |  | Primene 81-R | 1.0% | 28 |
|  | Alox ® 165 |  | — | 5.0% | 60 |

Example Q

HHPA Vs MHHPA with Four Hydrophobic Amines

In this example, mineral spirits was again used as the carrier solvent for 0.75 wt. % solutions of the test substances applied to R-36 panels. The results are shown in TABLE 31. For this coconut oil diglyceride, the results suggest that HHPA performs better than MHHPA as the anhydride cap and that the three primary amines outperform the secondary dibutylamine as the neutralizing base.

TABLE 31

Comparative Results for HHPA vs MHHPA with Four Hydrophobic Amines

| Test Substance | Glyceride | Anhydride Cap | Neutralizing Base | Days to Failure |
|---|---|---|---|---|
| 37G | CNTO-GLY | HHPA | Bu$_2$NH | 1.1 |
| 37H | 2:1 |  | octylamine | 2.0 |
| 37I |  |  | EHAM | 2.0 |
| 37J |  |  | Primene 81-R | 1.0 |
| 38G |  | MHHPA | Bu$_2$NH | 0.24 |
| 38H |  |  | octylamine | 1.0 |
| 38I |  |  | EHAM | 1.1 |
| 38J |  |  | Primene 81-R | 1.2 |

Dual-Use Corrosion Inhibitors

Example R

SYBO-Gly-HHPA 2:1:3 Various Amine Salts, Emulsion and Solvent Applied

Various amine salts from Example 35 were used both as emulsion-applied corrosion inhibitors at 5 wt. % in water and also as solvent-applied corrosion inhibitors at 0.75 wt. % in Exxsol® D-40 Fluid. Results are shown in TABLE 32. Where no test is indicated, either the aqueous emulsion did not have satisfactory stability, or the material was not totally soluble in the Exxsol® D-40. TABLE 32 shows several instances, however, of amine salts that exhibit both adequate emulsion stability and solvent solubility. These salts can therefore be used either as emulsion-applied corrosion inhibitors or as solvent-applied corrosion inhibitors. Aqualox® 2268S and Alox® 165 corrosion inhibitors at 10 wt. % and 5 wt. % respectively were used as comparative emulsion-type and solvent-type products. Test substances 35A, C, I, and J gave comparable or greater protection time under the test than these commercial products using both application methods, despite the lower use levels. This example also illustrates the influence of the amine neutralizing agent on the solubility properties of the corrosion inhibitor compounds as well as the protection time.

TABLE 32

Comparative results for SYBO-Gly-HHPA 2:1:3 with Various Amine Salts, Emulsion and Solvent Applied

| Test Substance | Neutralizing Amine | 5 wt. % in Water | | 0.75 wt. % in Exxsol D-40 ™ | |
|---|---|---|---|---|---|
|  |  | Coated Panel Appearance | Days to Failure | Coated Panel Appearance | Days to Failure |
| 35A | 3-amino-1-propanol | Mottled | >37 | Note a | 7 |
| 35B | 2-amino-2-methyl-1-propanol | Mottled | 21 | Not tested | — |
| 35C | 3-methoxypropylamine | Mottled | 28 | Note a | 7 |
| 35D | dimethylethanolamine | Mottled | >37 | Not tested | — |
| 35E | morpholine | Mottled | >37 | Not tested | — |
| 35F | methyldiethanolamine | Mottled | 28 | Note a | 3 |
| 35G | diethylethanolamine | Mottled | >37 | Not tested | — |
| 35H | 2-(2-aminoethoxy)ethanol | Mottled | 24 | Not tested | — |

TABLE 32-continued

Comparative results for SYBO-Gly-HHPA 2:1:3 with
Various Amine Salts, Emulsion and Solvent Applied

| Test Substance | Neutralizing Amine | 5 wt. % in Water | | 0.75 wt. % in Exxsol D-40 ™ | |
| --- | --- | --- | --- | --- | --- |
| | | Coated Panel Appearance | Days to Failure | Coated Panel Appearance | Days to Failure |
| 35I | 3-dimethylamino-1-propylamine | Mottled | >38 | Note a | 20 |
| 35J | t-butylamine | Mottled | 15 | Note a | 20 |
| 35K | cyclohexylamine | Not tested | — | Note a | 3 |
| 35L | 2-ethylhexylamine | Not tested | — | Note a | 20 |
| 35M | monoethanolamine | Mottled | 32 | Note a | 6 |
| 35N | triethanolamine | Mottled | 21 | Note a | 1 |
| | Aqualox ® 2268S, 10% in water | Uniform, slight edge dewetting | 9 | — | — |
| | Alox ® 165, 5% in Exxsol ™ D-40 Fluid | — | — | Uniform dark | 7 |

Note:
a. Uniform with ~1.3 cm darker band at bottom of panel.

Example S

SYBO-Gly-HHPA 2:1:3 Various Amine Salts, Solution Properties

The solution and emulsion properties of the materials shown in Example 35 are described in TABLE 33. The appearances of each material at 0.75 wt. % in Exxsol D-40™ fluid and of 5 wt. % emulsions in water are also noted. The amount of cream (volume %) on top of the emulsion was measured after centrifuging a portion of the emulsion for 10 minutes at 2500 rpm. A water separation test was performed on each of the 0.75 wt. % Exxsol D-40™ solutions. A 40-mL portion of the solution was combined with 10 mL of tap water in a 50-mL graduated cylinder which was inverted six times. The amount of time for 10 mL of aqueous layer to separate was noted along with the appearance of the aqueous and solvent layers. The results suggest that the solubility characteristics, both in organic solvents and as aqueous emulsions, are influenced by the choice of the amine neutralizing agent.

TABLE 33

SYBO-Gly-HHPA 2:1:3 Various Amine Salts. Solution Properties

| Test Substance | Amine | Appearance | | | Note |
| --- | --- | --- | --- | --- | --- |
| | | 0.75% in Exxsol ™ D-40 | 5% in H₂O | H₂O Sep. (sec) | |
| 35A | 3-amino-1-propanol | Clear | 2% Cream | 160 | a |
| 35B | 2-amino-2-methyl-1-propylamine | Turbid | 1% Cream | 248 | b |
| 35C | 3-methoxypropylamine | Clear | 3% Cream | 280 | c |
| 35D | dimethylethanolamine | Hazy | 2% Cream | 185 | b |
| 35E | morpholine | Hazy | 2% Cream | 180 | d |
| 35F | methyldiethanolamine | Clear | 1% Cream | 140 | a |
| 35G | diethylethanolamine | Hazy | 2% Cream | >300 | c |
| 35H | 2-(2-aminoethoxy)ethanol | Turbid | 1% Cream | 120 | a |
| 35I | 3-dimethylamino-1-propylamine | Clear | 1% Cream | 210 | e |
| 35J | t-butylamine | Clear | 2% Cream | 125 | f |
| 35K | cyclohexylamine | Clear | Separated | 210 | f |
| 35L | 2-ethylhexylamine | Clear | Separated | 60 | a |
| 35M | monoethanolamine | Clear | 1% Cream | 115 | a |
| 35N | triethanolamine | Clear | 1% Cream | 134 | a |

Notes:
a. Clear water and clear solvent.
b. Clear water. Solvent has fine droplets and ~5% hazy bottom layer.
c. Hazy water and turbid solvent.
d. Clear water and turbid solvent.
e. Clear water and clear solvent with stable foam cuff.
f. Clear water and turbid solvent with stable foam cuff.

As the examples illustrate, soybean oil transesterified with glycerin in a 2:1 mole ratio using dibutyltin dilaurate as a catalyst at 0.35 wt. % in the reaction mixture at a temperature of 180° C. yields a soy diglyceride mixture (Example 18) which when subsequently reacted with hexahydrophthalic anhydride at a mole ratio of about 0.90 moles of anhydride per mole of free hydroxyl groups in the diglyceride gives a soy diglyceride half-acid/half-ester having an acid number of about 74-75 mg KOH/g (Example 35). This half-ester/half-acid neutralized with monoethanolamine (Example 35M) gives a corrosion inhibitor organic salt that is soluble in organic solvents and also emulsifiable in water (Example S). Solutions or emulsions of this material containing from about 0.5 to 10 wt. % of the salt provide excellent thin-film rust protection to ferrous metals when exposed to atmospheric moisture (Example R).

The disclosures of all references mentioned herein are expressly incorporated herein by reference in their entireties.

The term "alkyl group" refers to a saturated, linear or branched group, which generally has between 1 and 24, e.g., between 1 and 16, typically between 1 and 14 carbon atoms and is bound to the rest of the molecule by a single bond, including, for example and not restricted to, methyl, ethyl, isopropyl, isobutyl, tert-butyl, heptyl, octyl, decyl, dodecyl, lauryl, hexadecyl, octadecyl, amyl, 2-ethylhexyl, 2-methylbutyl, 5-methylhexyl and similar.

The term "alkenyl group" refers to a linear or branched group, which generally has between 2 and 24, e.g., 2-16, typically 2-14 carbon atoms, with one or more carbon-carbon double bonds, conjugated or unconjugated, which is bound to the rest of the molecule by a single bond, including, for example and not restricted to, vinyl, oleyl, linoleyl and similar groups.

It will be appreciated that variants of the above-disclosed and other features and functions, or alternatives thereof, may be combined into many other different systems or applications. Various presently unforeseen or unanticipated alternatives, modifications, variations or improvements therein may be subsequently made by those skilled in the art which are also intended to be encompassed by the following claims.

What is claimed is:

1. A corrosion-inhibiting composition comprising a diluent and a mixture of organic salts of half ester-half acids having the general structure of STRUCTURE (1) at a total concentration of from 0.01-30 wt. % of the composition:

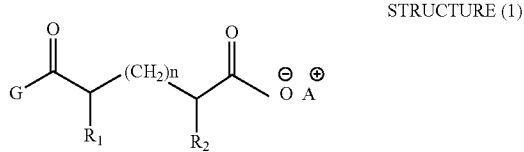

STRUCTURE (1)

where:
n is from 0-2;
G is a glyceride residue comprising a mixture of:

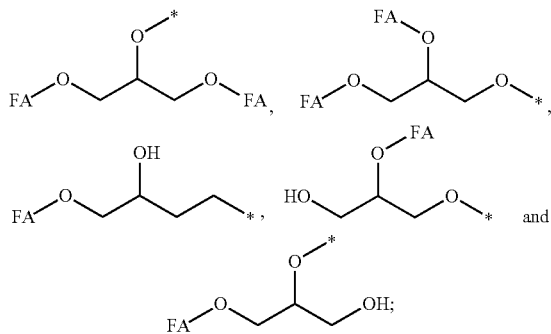

and each FA is a straight-chain fatty acyl residue having from 4 to 24 carbon atoms and from 0 to 3 double bonds in the carbon chain;
$R_1$ and $R_2$ are independently selected from hydrogen, straight-chain or branched alkyl or alkenyl groups having from 1-18 carbon atoms or where $R_1$ and $R_2$ together with the two carbons atoms to which they attach and the —$(CH_2)_n$— group form a cyclic structure having at least 5 carbon atoms; and
A is a neutralizing group which comprises an ammonium ion or a protonated organic base selected from the group consisting of protonated amines, alkylamines, alkanolamines, imidazoles, alkylimidazoles, and combinations thereof.

2. The composition of claim 1, wherein n is 0.

3. The composition of claim 1, wherein the mixture of organic salts of half ester-half acids having the general structure of STRUCTURE (1) is at a total concentration of at least 1 wt. % of the composition.

4. The composition of claim 1, wherein the mixture of organic salts of half ester-half acids having the general structure of STRUCTURE (1) is at a total concentration of up to 10 wt. % of the composition.

5. The composition of claim 1, wherein the diluent is selected from water, volatile organic solvents, oils, and combinations thereof.

6. The composition of claim 5, wherein the volatile organic solvent is selected from aliphatic and aromatic hydrocarbons, alcohols, glycols, toluene, terpenoids, terpenes, esters, ethers, acetals, polar aprotic solvents, ketones, and derivatives and combinations thereof.

7. The composition of claim 1, wherein the composition is in the form of an emulsion.

8. The composition of claim 1, wherein the diluent is present in the composition at a total concentration of at least 50 wt. %.

9. The composition of claim 1, wherein at least some of the fatty acyl residues are derived from a vegetable oil.

10. The composition of claim 9, wherein the vegetable oil has less than 20 wt. % saturated fatty acids.

11. The composition of claim 1, wherein the fatty acyl residues have an average of greater than 14 carbon atoms.

12. The composition of claim 1, wherein the protonated organic base comprises a protonated amine.

13. The composition of claim 1, wherein the protonated organic base is selected from the group consisting of 2-(2-aminoethoxy)ethanol; 5-amino-1-pentanol; 3-amino-1-propanol; 2-(2-aminoethoxy)ethanol; N,N-diethylethanolamine; 3-dimethylamino-1-propylamine; N,N-dimethylethanolamine; monoethanolamine; 2-ethylhexylamine; imidazole; 3-isododecyloxy-1-propylamine; 3-methoxypropylamine; 1-methylimidazole; 2-methylimidazole; tributylamine; triethanolamine; triisopropanolamine; a mixture of $C_{10}$-$C_{15}$ tert-alkyl primary amines; and combinations thereof.

14. The composition of claim 1, wherein an average number of FA groups per glyceride residue G in the mixture is at least 1.

15. The composition of claim 1, wherein an average molecular weight of organic salts in the mixture is less than 1250 g/mole.

16. The composition of claim 1, wherein when n is 0, at least one of $R_1$ and $R_2$ is not hydrogen.

17. A corrosion-inhibiting composition comprising a diluent and a mixture of organic salts of half ester-half acids having the general structure of STRUCTURE (1) at a total concentration of from 0.01-30 wt. % of the composition:

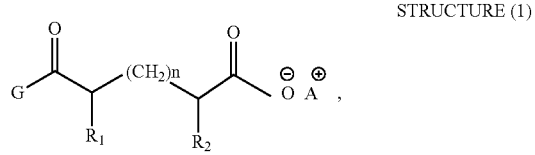

STRUCTURE (1)

where:
n is from 0-2;
G is a glyceride residue comprising a mixture of:

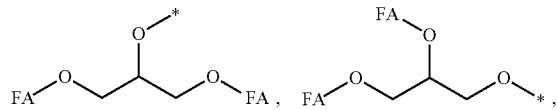

-continued

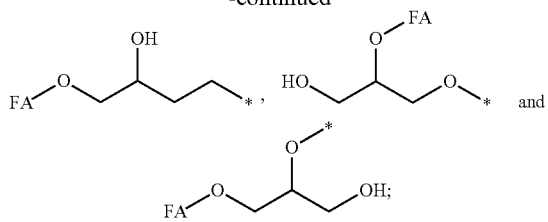

each FA is a straight-chain fatty acyl residue having from 4 to 24 carbon atoms and from 0 to 3 double bonds in the carbon chain, wherein at least some of the fatty acyl residues are derived from an unhydrogenated vegetable oil;

$R_1$ and $R_2$ are independently selected from hydrogen, straight-chain or branched alkyl or alkenyl groups having from 1-18 carbon atoms or where $R_1$ and $R_2$ together with the two carbons atoms to which they attach and the —$(CH_2)_n$— group form a cyclic structure having at least 5 carbon atoms; and A is a neutralizing group.

18. The composition of claim 17, wherein the neutralizing group comprises at least one of a protonated organic base, a metal cation, and an ammonium ion.

19. The composition of claim 18, wherein the neutralizing group comprises a protonated organic base selected from the group consisting of protonated amines, alkylamines, alkanolamines, imidazoles, alkylimidazoles; and combinations thereof.

20. A method of inhibiting corrosion of a metallic surface in contact with a corrosive environment, the method comprising:

contacting the surface with a corrosion-inhibiting composition comprising a diluent and a mixture of organic salts of half ester-half acids having the general structure of STRUCTURE (1) at a total concentration of from 0.01-30 wt. % of the composition:

STRUCTURE (1)

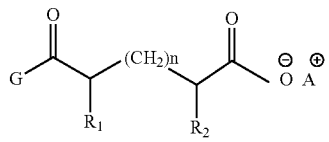

where:
n is from 0-2;
G is a glyceride residue comprising a mixture of:

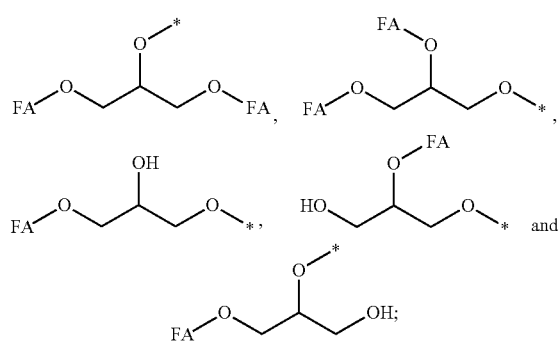

each FA is a straight-chain fatty acyl residue having from 4 to 24 carbon atoms and from 0 to 3 double bonds in the carbon chain;

$R_1$ and $R_2$ are independently selected from hydrogen, straight-chain or branched alkyl or alkenyl groups having from 1-18 carbon atoms or where $R_1$ and $R_2$ together with the two carbons atoms to which they attach and the —$(CH_2)_n$— group form a cyclic structure having at least 5 carbon atoms; and A is a neutralizing group.

21. A method for forming a corrosion-inhibiting composition comprising:

reacting a triglyceride of the general structure:

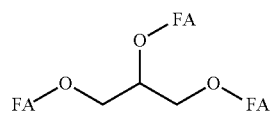

with glycerin in the presence of a transesterification catalyst to form a glyceride mixture, where each FA is a straight-chain fatty acyl residue having from 4 to 24 carbon atoms and from 0 to 3 double bonds in the carbon chain;

reacting the glyceride mixture with a cyclic carboxylic acid anhydride;

with a neutralizing base, neutralizing the product of the reaction of the glyceride mixture with the cyclic carboxylic acid anhydride; and combining the neutralized reaction product with a diluent to form the corrosion-inhibiting composition, wherein the neutralized reaction product is at a total concentration of from 0.01-30 wt. % of the composition.

22. The method of claim 21, wherein the cyclic carboxylic acid anhydride has the structure general structure of STRUCTURE (3):

STRUCTURE (3)

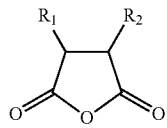

where $R_1$ and $R_2$ are independently selected from hydrogen, straight-chain or branched alkyl or alkenyl groups having from 1-18 carbon atoms or where $R_1$ and $R_2$ together form a cyclic structure having at least 5 carbon atoms.

23. A mixture of organic salts of half ester-half acids having the general structure of STRUCTURE (1):

STRUCTURE (1)

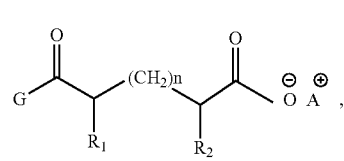

where:
  n is from 0-2;
  G is a glyceride residue comprising a mixture of:

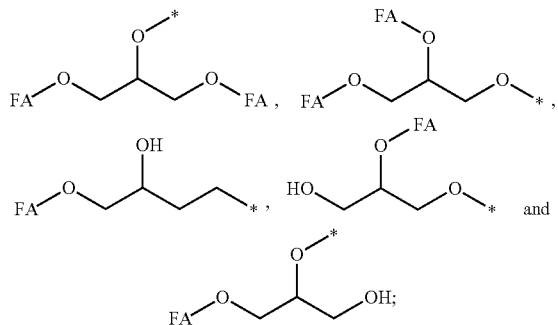

each FA is a straight-chain fatty acyl residue having from 4 to 24 carbon atoms and from 0 to 3 double bonds in the carbon chain;

$R_1$ and $R_2$ are independently selected from hydrogen, straight-chain or branched alkyl or alkenyl groups having from 1-18 carbon atoms or where $R_1$ and $R_2$ together with the two carbons atoms to which they attach and the —$(CH_2)_n$— group form a cyclic structure having at least 5 carbon atoms; and A is a neutralizing group, which comprises an ammonium ion or a protonated organic base selected from the group consisting of protonated amines, alkylamines, alkanolamines, imidazoles, alkylimidazoles; and combinations thereof.

24. A corrosion-inhibiting composition comprising:
  an emulsion comprising:
    at least 70 wt. % of a diluent comprising at least one of water and an organic solvent; and
    0.01-30 wt. % of a mixture of organic salts of half ester-half acids having the general structure of STRUCTURE (1) at a total concentration of from 0.01-30 wt. % of the composition:

STRUCTURE (1)

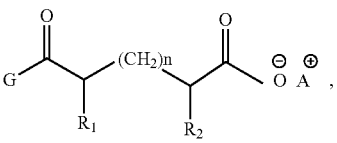

where:
  n is from 0-2;
  G is a glyceride residue comprising a mixture of:

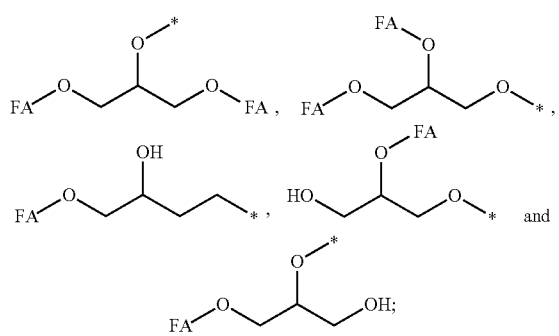

each FA is a straight-chain fatty acyl residue having from 4 to 24 carbon atoms and from 0 to 3 double bonds in the carbon chain;

$R_1$ and $R_2$ are independently selected from hydrogen, straight-chain or branched alkyl or alkenyl groups having from 1-18 carbon atoms or where $R_1$ and $R_2$ together with the two carbons atoms to which they attach and the —$(CH_2)_n$— group form a cyclic structure having at least 5 carbon atoms; and A is a neutralizing group.

* * * * *